United States Patent
Atta et al.

(10) Patent No.: US 9,828,445 B1
(45) Date of Patent: Nov. 28, 2017

(54) SYNTHESIS OF MODIFIED CHITOSAN PARTICLES FOR ORAL INSULIN DELIVERY

(71) Applicant: KING SAUD UNIVERSITY, Riyadh (SA)

(72) Inventors: Ayman M. Atta, Cairo (EG); Hamad A. Al-Lohedan, Riyadh (SA); Abdelrahman O. Ezzat, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/378,017

(22) Filed: Dec. 13, 2016

(51) Int. Cl.
| | |
|---|---|
| *A61K 47/36* | (2006.01) |
| *C08B 37/08* | (2006.01) |
| *C08F 251/00* | (2006.01) |
| *A61K 38/28* | (2006.01) |
| *A61K 47/32* | (2006.01) |

(52) U.S. Cl.
CPC .......... *C08B 37/003* (2013.01); *A61K 38/28* (2013.01); *A61K 47/32* (2013.01); *A61K 47/36* (2013.01); *C08F 251/00* (2013.01)

(58) Field of Classification Search
None
See application file for complete search history.

(56) References Cited

FOREIGN PATENT DOCUMENTS

| | | |
|---|---|---|
| CN | 102120781 | 7/2011 |
| KR | 20110026280 | 3/2011 |

OTHER PUBLICATIONS

Gupta et al., "Controlled-Release Formulations for Hydroxy Urea and Rifampicin Using Polyphosphate-Anion-Crosslinked Chitosan Microspheres" Journal of Applied Polymer Science (2007) vol. 104 pp. 1942-1956.*
Hu et al., "Shell cross-linked stearic acid grafted chitosan oligosaccharide self-aggregated micelles for controlled release of paclitaxel" (2006) vol. 50 pp. 97-103.*
Li et al., "Antitumor drug Paclitaxel-loaded pH-sensitive nanoparticles targeting tumor extracellular pH" (2009) vol. 77 pp. 773-778.*
Zhang et al., "Temperature and pH-responsive polymeric composite membranes for controlled delivery ofproteins and peptides" Biomaterials (2004) vol. 25 pp. 5281-5291.*
Cho et al., "Preparation, Characterization, and Protein Loading Properties of N-Acyl Chitosan Nanoparticles" Journal of Applied Polymer Science (2012) vol. 124 pp. 1366-1371.*
Shelma et al., "Acyl modified chitosan derivatives for oral delivery of insulin and curcumin" J Mater Sci Mater Med (2010) vol. 21 pp. 2133-2140.*

* cited by examiner

*Primary Examiner* — Eric S Olson
(74) *Attorney, Agent, or Firm* — Richard C. Litman

(57) ABSTRACT

Synthesis of modified chitosan particles for oral insulin delivery includes amidation of chitosan with a fatty acid, a modified fatty acid, and/or an amino acid. The amidated chitosan can be grafted with N-isopropylacrylamide (NIPAm) and cross-linked to provide the modified chitosan particles.

12 Claims, 28 Drawing Sheets

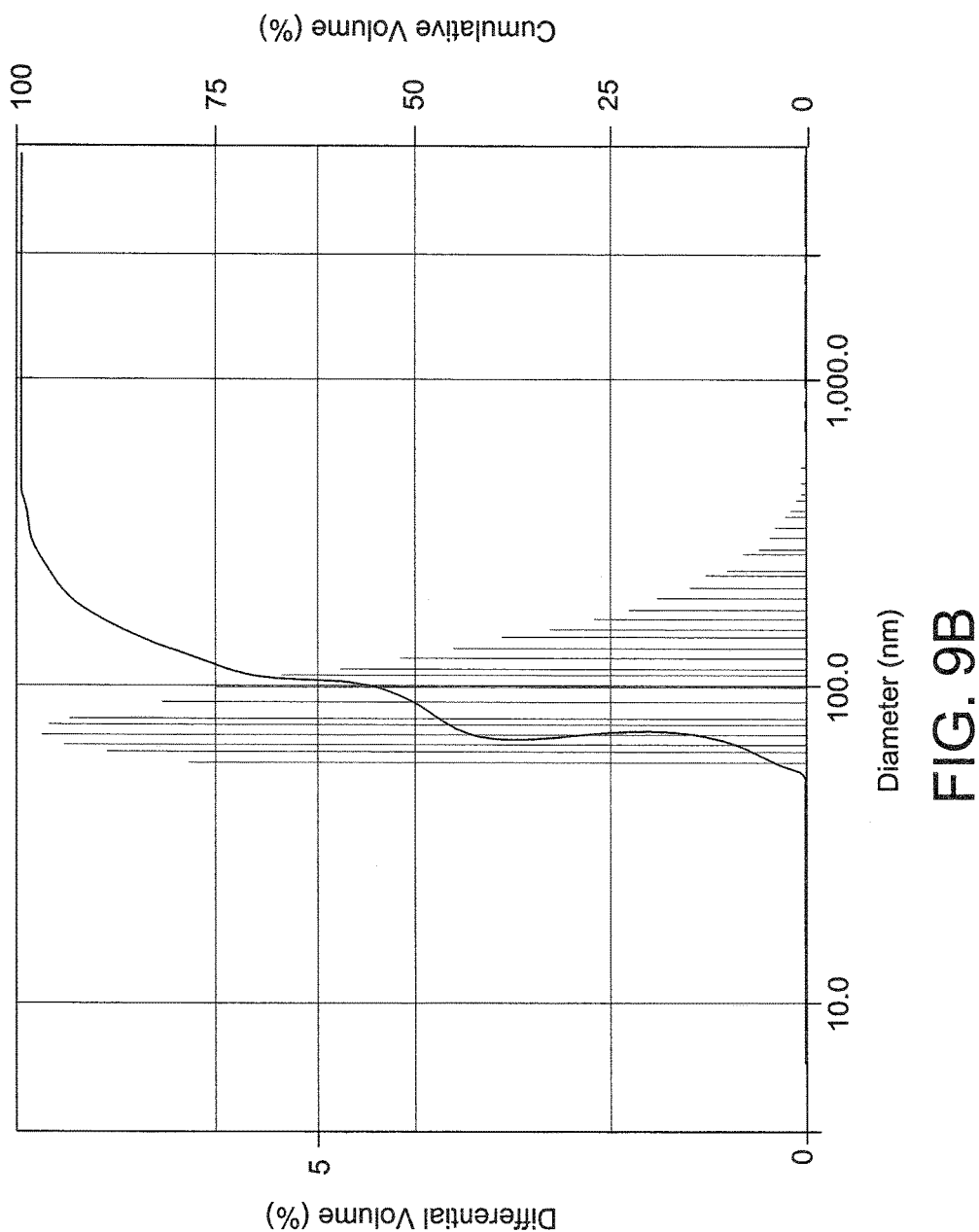

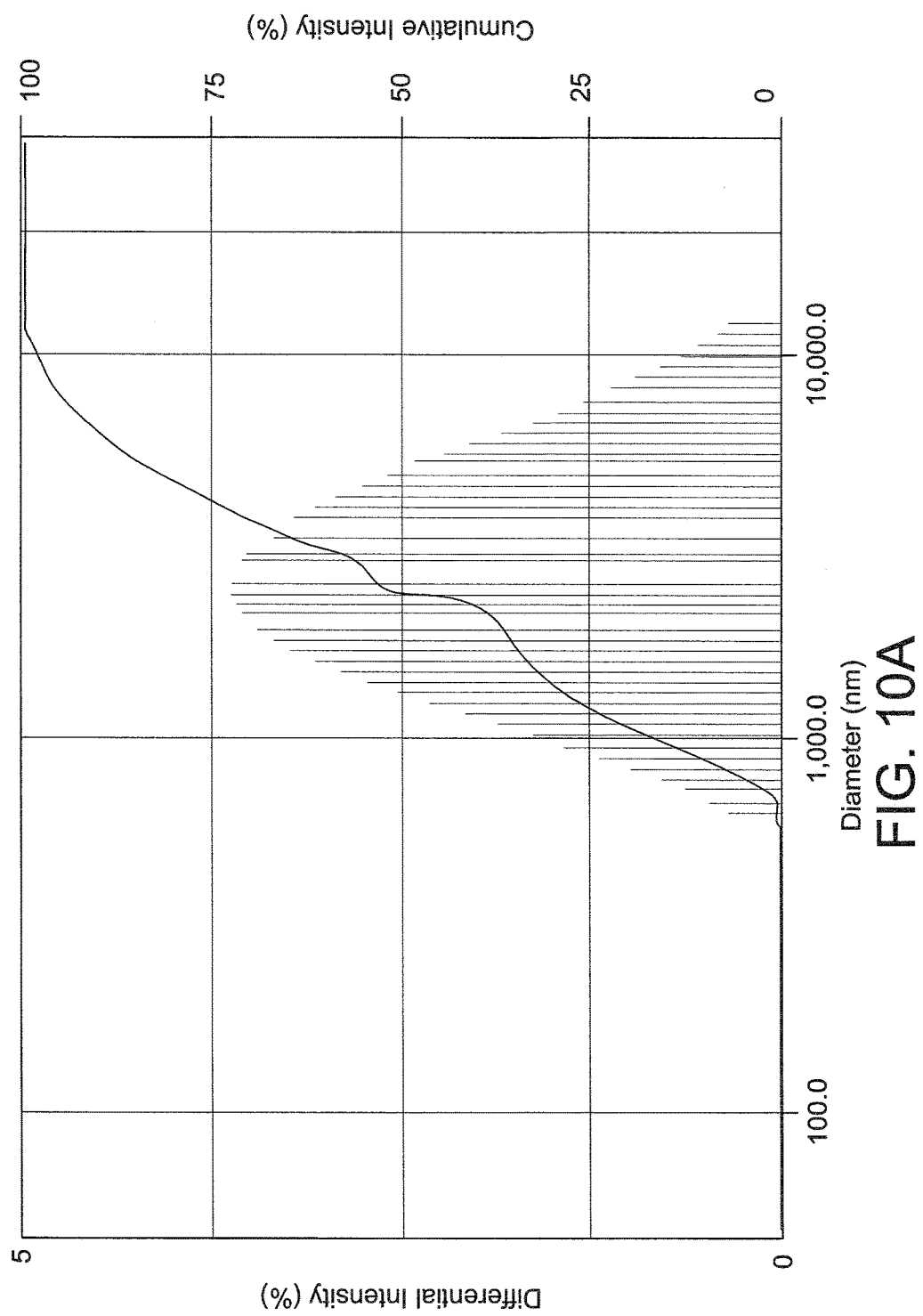

SYNTHESIS OF MODIFIED CHITOSAN PARTICLES FOR ORAL INSULIN DELIVERY

BACKGROUND OF THE INVENTION

1. Field of the Invention

The present invention relates generally to synthesis of micro and nanoscale size particles for drug delivery, and particularly, to a method of preparing modified chitosan particles for oral insulin delivery.

2. Description of the Related Art

It is well known that insulin is essential for type 1 and advanced type 2 diabetics to maintain blood glucose levels. In 2015, 402 million people throughout the world suffered from diabetes. It is expected that the number of diabetics will increase to 592 million by 2035. Diabetics injected with insulin often suffer from pain, tenderness, local tissue necrosis, microbial contamination and nerve damage due to continuous injection. It was previously recommended that natural polymers at micro and nanoscale sizes are preferred for oral drug delivery due to non-toxicity and good biological and anti-microbial activity.

Chitosan (CS), as a natural polysaccharide, possesses valuable properties including biocompatibility, biodegradability and non-toxicity. As such, chitosan has been used as a natural polymer for insulin release. Obtaining monodisperse nanoparticles based on ionic gelation using sodium tripolyphosphate has been previously reported. Different types of polymeric chitosan nanoparticles have been tested in in vitro and in vivo studies in diabetic animal models. However, natural CS is water-insoluble at alkaline and neutral pH, a result of its amino group deprotonation, causing the impairment of its mucoadhesiveness at pH 7.4. Introduction of trimethyl groups onto the structure of CS has been shown to highly improve the water-solubility of CS due to the relatively easier protonation of the quaternary amine groups. It was also reported that pH-responsive nanoparticles consisting of CS and poly(g-glutamic acid) (PGA) for oral delivery of insulin showed a higher stability over a broader pH range from 2.0 to 7.2.

Thus, modified chitosan nanoparticles for delivering oral insulin for treating diabetes thereby solving the aforementioned problems is desired.

SUMMARY OF THE INVENTION

Synthesis of modified chitosan particles for oral insulin delivery includes amidation of chitosan with a fatty acid, a modified fatty acid, and/or an amino acid. The amidated chitosan can be grafted with N-isopropylacrylamide (NIPAm) and cross-linked to provide the modified chitosan particles.

These and other features of the present invention will become readily apparent upon further review of the following specification and drawings.

BRIEF DESCRIPTION OF THE DRAWINGS

FIG. 9A-C shows the DLS measurement of CSG-NIPAm crosslinked with MBA at 25° C. in water.

FIG. 10A-C shows the DLS measurement of CSOMA-NIPAm crosslinked with TPP at 25° C. in water.

Similar reference characters denote corresponding features consistently throughout the attached drawings.

DETAILED DESCRIPTION OF THE PREFERRED EMBODIMENTS

Synthesis of modified chitosan particles for oral insulin delivery can include amidation of chitosan with a fatty acid, a modified fatty acid, and/or an amino acid. The amidated chitosan can be grafted with N-isopropylacrylamide (NIPAm) and cross-linked to provide the modified chitosan particles. The modified chitosan particles can include chitosan particles in nano or microscale sized. Modified chitosan nanoparticles can have a mean particle diameter of about 40 nm to about 150 nm, for example. The modified chitosan particles achieve slow insulin release in stomach fluids without significant aggregation in bile salts.

Chitosan (CS) is soluble in the acidic condition and cannot be used directly without modification in oral drug delivery. Synthesis and characterization of amphiphilic CS nanoparticles based on chitosan (CS) as natural product is described herein. As described below, the chemical structure of CS was modified with fatty acids or amino acids in the presence of EDC (1-ethyl-3-(3-dimethylaminopropyl) carbodiimide hydrochloride) and a catalyst to alter its hydrophilic character. The high surface active materials produce amphiphilic materials having a tendency to orient themselves at the interfaces to form self-assembled materials.

Figure 1:
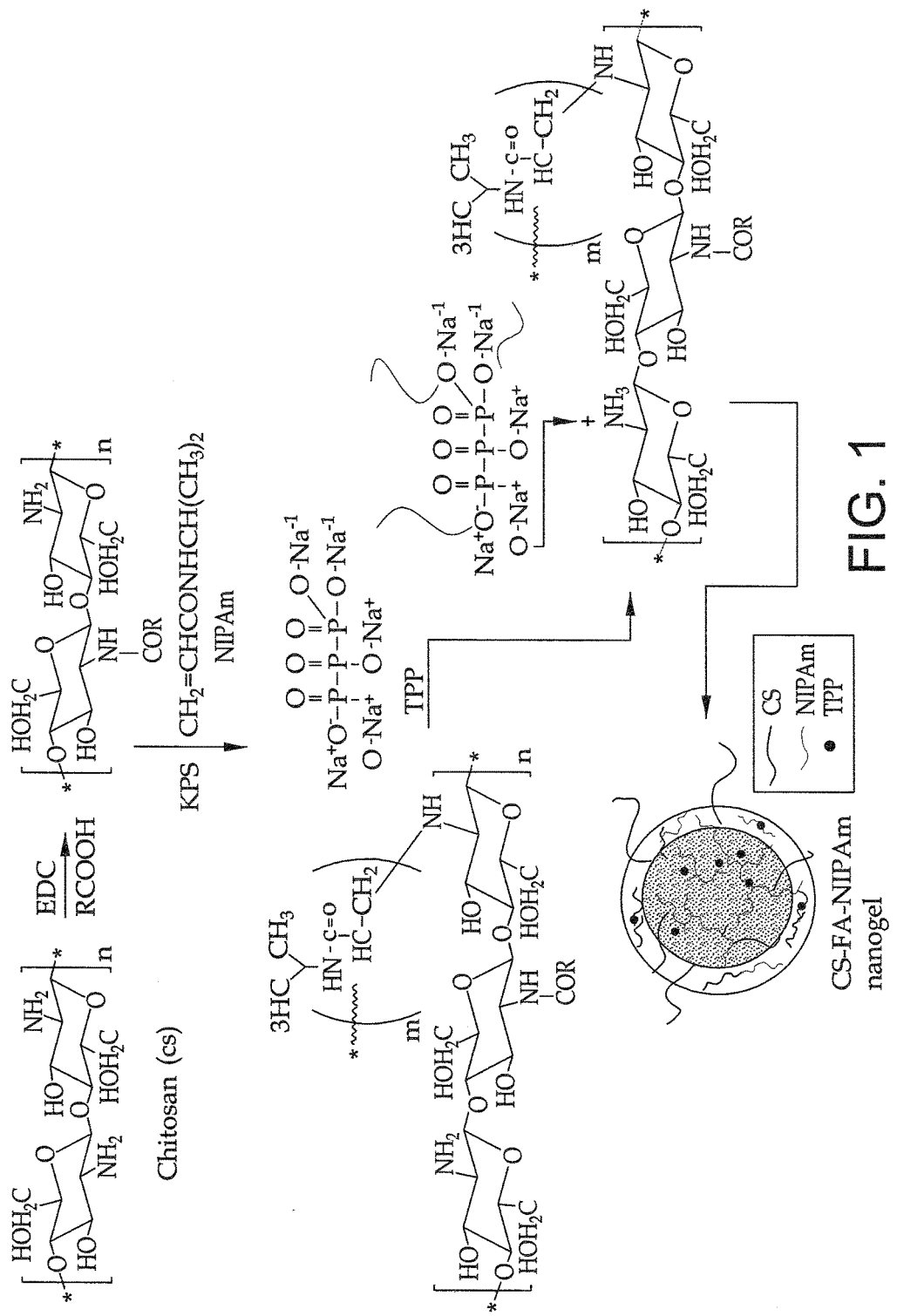
FIG. 1 shows the synthesis of chitosan polymeric nanoparticle using ion gelation technique.
Figure 2:
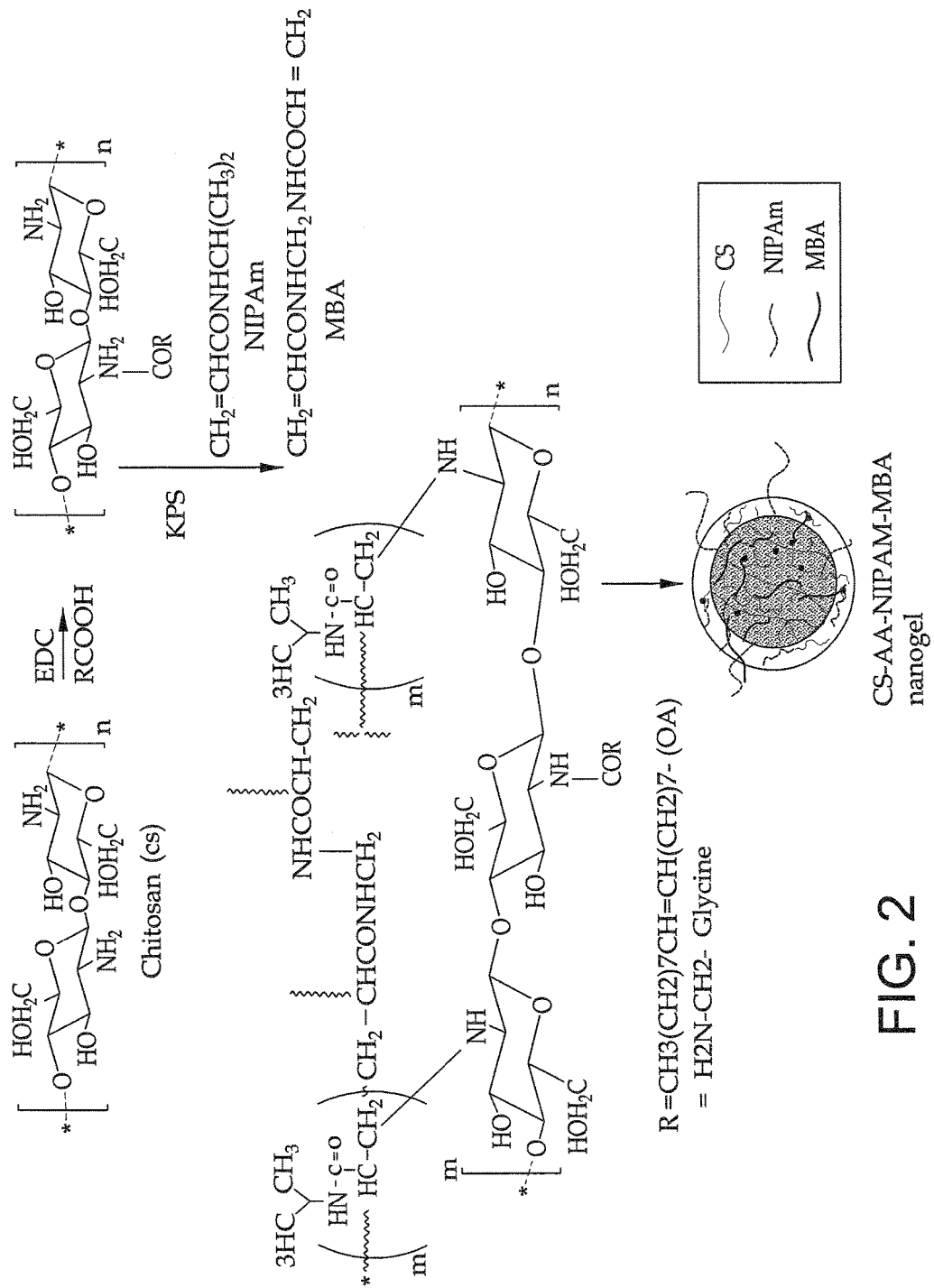
FIG. 2 shows the synthesis of chitosan (CS) polymeric nanoparticle using radical crosslinking above LCST technique.

EDC can be used to form chitosan amide using OA and LOA as illustrated in FIG. 1. In the examples described below, the yields of CSOA and CSLA were 78% and 89% (W/W), respectively. The high yield of CSLA can be attributed to high reactivity and compatibility between LOA and CS which increased by increment the unsaturation degree that increased with incorporation of LOA instead of OA. On the other hand, amino acids such as glycine were used to from chitosan amide to increase the sensitivity of modified chitosan with amino acids to pH variations due to the presence of amine groups. The yields of amidated CS with amino acids ranged between 90% and 99% due to higher compatibility between reactants in amino acids more than fatty acids. The sensitivity of chitosan to environmental conditions such as temperature and pH can be modified by grafting the CS with alkyl acrylamides such as NIPAm. The schemes of the methods are represented in FIGS. 1 and 2. The modified chitosan polymer with fatty, amino acids and NIPAm can be converted to micro or nanoscale by ionic gelation with TPP or with crosslinking radical polymerization above lower critical solution transition temperature (LCST) above 45° C. as illustrated in FIGS. 1-2.

The amidated chitosan can include compounds of Formula I:

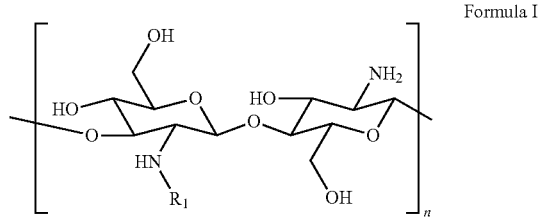

Formula I wherein "n" is an integer ranging from 10 to 10000, and $R_1$ is independently selected from the group consisting of an amino acid, oleic acid, linoleic acid, linoleinc acid, and oligo maleic anhydride group.

Chitosan can be amidated with an amino acid or a fatty acid, such as oleic acid (OA), linoleic acid (LOA), linoleinc acid (LNA), or oligo maleic anhydride The amidation of the chitosan includes dissolving the chitosan in 1% aqueous acetic acid solution and adding methanol to the solution. A methanolic solution of the fatty acid or amino acid can be added to the chitosan solution to provide a reaction mixture. An activating agent can be added dropwise into the reaction mixture to couple the fatty acid or amino acid with the chitosan and form a fatty acid or an amino acid coupled chitosan. The activating agent can be 1-ethyl-3-(3-dimethylaminopropyl)carbodiimide (EDC). In the reaction, a mole ratio of the fatty acid or an amino acid to the crosslinking agent can be about 1:1. The reaction mixture is added to a methanol/ammonia (70/30, v/v) solution to form a precipitate. The precipitate is isolated by filtration. The precipitate can be washed, e.g., with distilled methanol or ether, and dried under vacuum.

The precipitate or amidated chitosan can be grafted with N-Isopropyl acrylamide (NIPAm) to form compounds of Formula II:

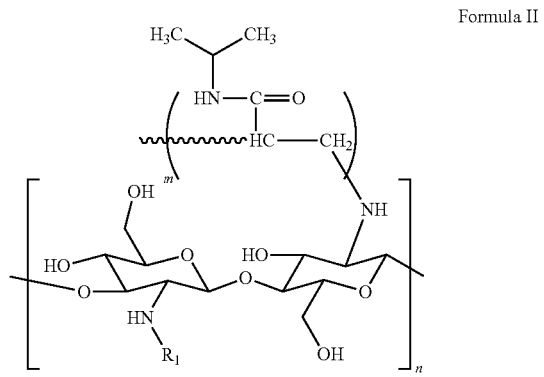

Formula II where "n" is an integer ranging from 10 to 10000; "m" is an integer ranging from 1 to 10000; $R_1$ is selected from the group consisting of an amino acid, oleic acid, linoleic acid, linoleinc acid, and oligo maleic anhydride group.

Compounds of Formula II (NIP-Am grafted, amidated chitosan) can be prepared by combining the amidated chitosan with N-Isopropyl acrylamide (NIPAm) in water to form an aqueous reaction mixture; adding an organic solvent dropwise to the aqueous reaction mixture; heating the aqueous reaction mixture under constant stirring, and centrifuging the reaction mixture to isolate a precipitate. The precipitate can be washed and dried in the oven. The organic solvent can be 3-aminopropyltriethoxyxilane (APS). The centrifuging step can occur at a speed of 20000 rpm for about 15 min at a temperature of about 20° C.

The amidated chitosan is cross-linked to form modified chitosan in micro or nanoscale. The amidated chitosan can be cross-linked using radical crosslinking with N,N-methylene bisacrylamide (MBA) or by crosslinking using ionic gelation with sodium tripolyphosphate 8% w/v solution (TPP). For radical crosslinking with MBA, NIP-Am, CS, and MBA can be dissolved in water and mixed with an organic solvent such as APS. After raising the reaction temperature for a period of time, the mixture can be centrifuged to isolate the precipitate. The centrifuging step can occur at a speed of 20000 rpm for about 15 min at a temperature of about 20° C. For ionic gelation, compounds of Formula II can be dissolved in 0.1M acetic acid solution. Methylene chloride can be added to the solution until formation of a turbid solution. A crosslinking agent, such as sodium tripolyphosphate 8% w/v solution (TPP), can be added under stirring at ambient temperature until nanoparticles are formed. The mixture can be centrifuged to isolate the nanoparticles. The centrifuging step can occur at a speed of 20000 rpm for about 15 min at a temperature of about 20° C.

Insulin can be loaded onto the modified chitosan particles by mixing the modified chitosan articles with insulin to form a mixture, incubating the mixture at a time and temperature sufficient to adsorb the insulin onto the particles, and centrifuging the mixture to isolate the particles.

As described herein, the chemical structure of chitosan was improved with modified and unmodified unsaturated fatty acid with different degrees of amidation. Chitosan was reacted with different types of amino acids to change the pH sensitivity of amidiated chitosan. The modified chitosan products were modified with alkyl acrylate and alkyl acrylamides to modify the thermal sensitivity of chitosan polymers. The modified chitosan grafts were crosslinked in nano or micro-scale in the presence of sodium polyphosphates to increase their pH and temperature sensitivity in synthetic stomach fluid and bile salts. The chemical structures of modified chitosan polymers were determined by FTIR and NMR analyses. In-vitro insulin loading and release in synthetic stomach fluid and bile salt solution at pH ranged from 1.5 to 7.4 were determined and achieved valuable results to apply the modified chitosan nano and microgels as oral insulin tablets.

As used herein the term "Nanoparticle" refers to a particle having at least one dimension and sized between 1 and 100 nanometers. The nanoparticles can include nanoparticles and nanotubes. In some embodiments, the nanoparticles disclosed herein are from about 100 nm to about 1000 nm in diameter, e.g., 100 to 500 nm.

The examples which follow will further illustrate the process of preparing the modified chitosan particles and use of the modified chitosan particles as an insulin delivery vehicle.

The following materials were used in the examples. Insulin NovoRapid® (each ml contain 100 unit of insulin as part (3.5 mg)) was used as insulin source. Fatty acids (FA) such as oleic acids (OA) having the formula "$CH_3(CH_2)_7CH=CH(CH_2)_7COOH$", linoleic acid (LOA) having the formula, "$CH_3(CH_2)_4CH=CHCH_2CH=CH(CH2)_7CO_2H$" and linoleinc acid (LNA) having the formula, "$CH_3CH_2CH=CHCH_2CH=CHCH_2CH=CH(CH_2)_7CO_2H$", were purchased from Aldrich chemicals Co. and used as received or modified by fusion with maleic anhydride (MA) at mol ratio of 4:1 for 3 h at 200° C. and purified by heating at 900° C. under vacuum for 4 hr to remove the excess of MA to obtain OMA. Amino acids such as Glycine, Alanine, Valine, Leucine, Isoleucine, Serine, Cysteine, Selenocysteine, Threonine, Methionine, Proline, Phenylalanine, Tyrosine Tryptophan, Histidine, Lysine, Arginine, Aspartate, Glutamate, Asparagine and Glutamine were purchased from Merck and used as received. Chitosan (CS) of 100 mesh, degree of deacetylation 90%, molecular weight 28 KDa, was made from crab shell and 1-ethyl-3-(3-dimethylaminopropyl) carbodiimide (EDC), sodium tripolyphosphate (TPP), N-isopropylacrylamide (NIPAm), potassium persulfate (KPS) and N,N-methylene bisacrylamide (MBA) were obtained from Aldrich Chemicals Co.

The synthetic stomach fluid was prepared using deionized distilled (DDI) water and contained HCl (0.42 M) and glycine (0.40 M) at pH of 1.5. Bile salts based on glycocholate (24%), glycochenodeoxycholate (24%), taurocholate (12%), glycodeoxycholate (16%), taurodeoxycholate (8%) and lithocholate (4%) were used to study the insulin release at pH 7.4. Phosphate buffer solution with ionic strength 0.1 M having different pH were used to study the effect of pH on both the zeta potential and insulin release.

Example 1

Amidation of Chitosan (CS) with Fatty, Modified Fatty Acids and Amino Acids (AA)

For amidating chitosan (CS) with OA, LOA, LNA or OMA using EDC as a catalyst, CS (1 g) was dissolved in 100 ml of 1% aqueous acetic acid solution. Methanol (85 mL) was added dropwise to the reaction mixture with stirring. The OA, LOA, LNA or OMA was dissolved in methanol and added to the CS solution at 0.34 mol/mol glucosamine residue. EDC (15 mL) dissolved in methanol (0.07 g/L) was added dropwise to the reaction mixture with stirring at room temperature. The molar ratios of OA, LOA, LNA or OMA to DEC was 1. The reaction mixture was stirred for 24 hrs at room temperature and poured into 200 mL of methanol/ammonia solution (70/30, v/v) while stirring. The precipitate was filtered, washed with distilled methanol, ether and dried under vacuum for at 20° C. The same procedure was repeated for amidation of amino acids instead of fatty acids.

Example 2

Grafting of Amidated Chitosan (CS) with NIPAm

Amidated chitosan (CS) with fatty or amino acids (0.2 g) and N-Isopropylacrylamide (NIPAm) (1.2 g) were dissolved in 50 ml deionized water (DW) and added drop wise to 50 ml (0.08 g APS) at 60° C. for interval of 2 h. The reaction temperature was raised to 70° C. under nitrogen bubbling and remained constant under stirring for another 2 h. The reaction mixtures were centrifuged for 15 min at 20° C. at a speed of 20,000 rpm. The supernatant was discarded, and the articles were washed severally with water and dried in a vacuum oven at 20° C. for 24 h. The CS amidated with OA, LOA, LNA, OMA, glycine and grafted with NIPAm are abbreviated herein as CSOA-NIPAm, CSLOA-NIPAm, CSLNA-NIPAm, CSOMA-NIPAm and CSG-NIPAm, respectively.

Example 3

Preparation of Modified Chitosan: Crosslinking with MBA

Crosslinked CS-NIPAm was prepared using radical crosslinking as follows. NIPAm (1.2 g), CS (0.2 g) and N,N-methylene bisacrylamide, MBA (0.03 g) were dissolved in 50 ml deionized water and mixed dropwise to 50 ml (0.08 g APS) at 60° C. for interval of 2 h. Reaction temperature was raised to 70° C. and the reaction continued for another 2 h. The mixture was centrifuged for 15 min at 20° C. at a speed of 20000 rpm. The supernatant was discarded and the particles washed severally with water, and dried in a vacuum oven at 20° C. for 24 h. The same procedure was repeated using CSOA, CSLOA, CSLNA, CSOMA or CSG instead of CS to prepare crosslinked CSOA-NIPAm, CSLOA-NIPAm, CSLNA-NIPAm, CSOMA-NIPAm and CSG-NIPAm nanogels.

Example 4

Preparation of Modified Chitosan: Crosslinking Using Ionic Gelation with TPP

CSOA-NIPAm, CSLOA-NIPAm, CSLNA-NIPAm, CSOMA-NIPAm or CSG-NIPAm grafts (0.5 g) was dissolved in 100 mL of 0.1 M acetic acid solution. Methylene chloride was added to the reaction mixture until formation of a turbid solution. Sodium tripolyphosphate (TPP) 20 mL (8% w/v solution) was added with constant stirring at ambient temperature for 2 h under vigorous stirring. The mixture was centrifuged for 15 min at 20° C. at a speed of 10000 rpm. The supernatant was discarded and the microparticles washed severally with water and then dried in a vacuum oven at 20° C. for 24 h.

Example 5

Loading of Insulin onto the Nanogels

Modified chitosan (CS) nanoparticles (20 mg) were mixed with insulin solution (30 mg/mL), vortexed and incubated at 37° C. for 24 h. After adsorption, the suspension was centrifuged at 10,000 g for 5 min and free insulin was measured in the supernatant by using UV spectrophotometer at 280 nm. All experiments were done in triplicate to calculate encapsulation efficiency (EE) by the following formula:

$$EE(\%) = \frac{[(\text{Total amount of insulin}) - (\text{free insulin in supernatant})]}{\text{Total Amount of Insulin}} \times 100 \qquad (1)$$

The amount of insulin adsorption at equilibrium Q (mg/g) was calculated from the following equation:

$$Q = [(C_o - C_e) \times V/(m)] \quad (2)$$

Where $C_o$ and $C_e$ (mg/L) are the liquid phase concentrations of insulin at initial and equilibrium, respectively, V (L) the volume of the solution and m (g) is the mass of nanogels used.

Example 4

In Vitro Insulin Release Profile

To determine the insulin release profiles from modified CS/insulin self-assembled nanoparticles, test samples were immersed in buffer solutions at different pH corresponding to GI tract (i.e., pH 1.5, pH 6.8 and pH 7.4) with mild agitation. At specific time intervals, the samples were centrifuged and an aliquot from each sample was taken out. The concentration of the released insulin in the aliquot of each sample was determined using UV spectrophotometer at 280 nm. The effect of contact time on the sorption was studied in different time intervals ranging from 30 min to 240 min.

Figure 3A:
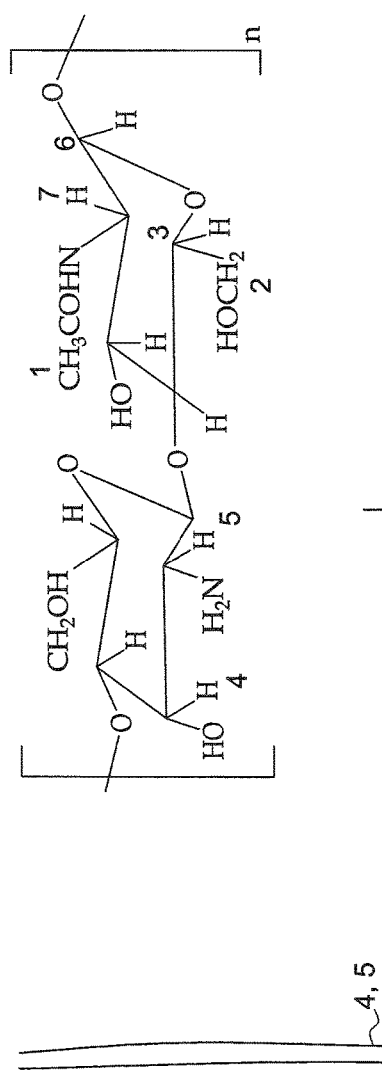
FIG. 3A-B shows the $^1$H-NMR spectra of chitosan (CS) and chitosan-linoleic acid (CSLA) respectively.
Figure 3A:
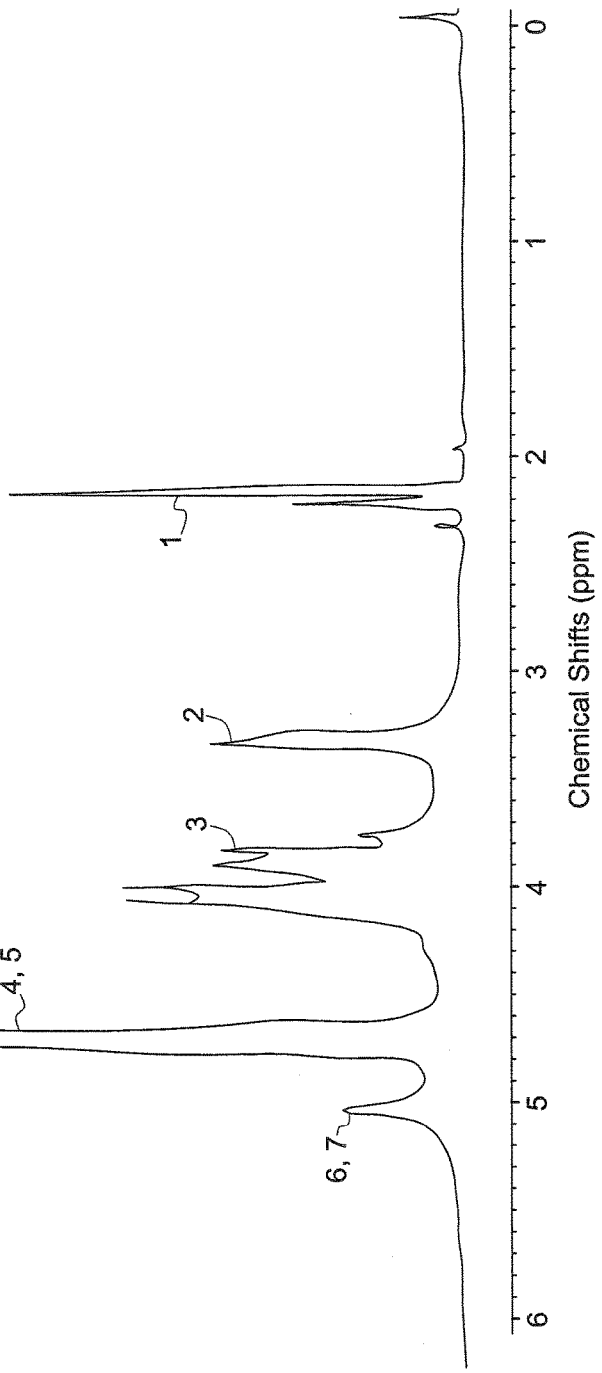
Figure 3B:
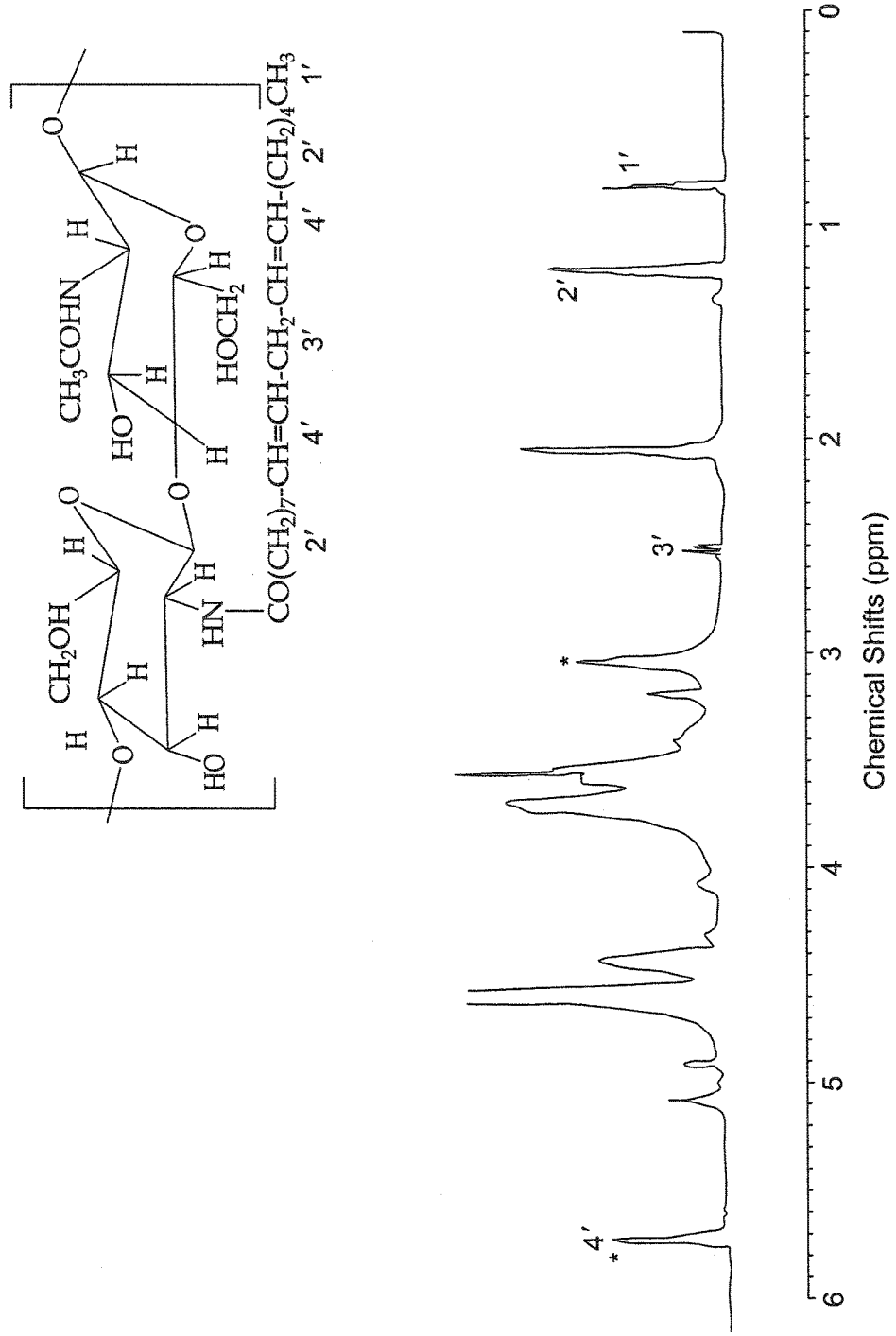

The chemical structure of the modified chitosan nanoparticles was investigated using $^1$H-NMR. The 1H-NMR analyses was used here to determine the degree of CS amidation with OA and LOA. In this respect, the $^1$H-NMR spectra of CS, CSOA and CSLA are represented in FIGS. 3A-3B. The amidation content of the CS was determined using $^1$H-NMR to calculate the ratio of CH=CH groups in the oleyl substituent (δ 5.3, 2H of OA and 4H of LA) to the CS methylene group (CH2-OH, δ 3.2 ppm, 4H). The amidation percentages of CS with OA and LA were determined as 45.3 and 55.6%. The amidation of CS with glycine was 75.3%. These data indicated that the increment degree of unsaturation in fatty acid and presence of amino group in amino acids increased the compatibility between CS, glycine or LA due to increment of acid solubility in the reaction medium acidic water/isopropanol solvent. The incorporation of LA and OA onto CS amine group was confirmed by appearance of new peaks at 5.5 and 1.5 and 0.98 ppm which attributed to CH=CH, (CH2)n and $CH_3$, respectively. Typical peaks appeared in FIG. 3 of CSOA the ring methane and methylene protons of CS saccharide units and methylene groups of MPEG are similar to what was reported previously.

Figure 4:
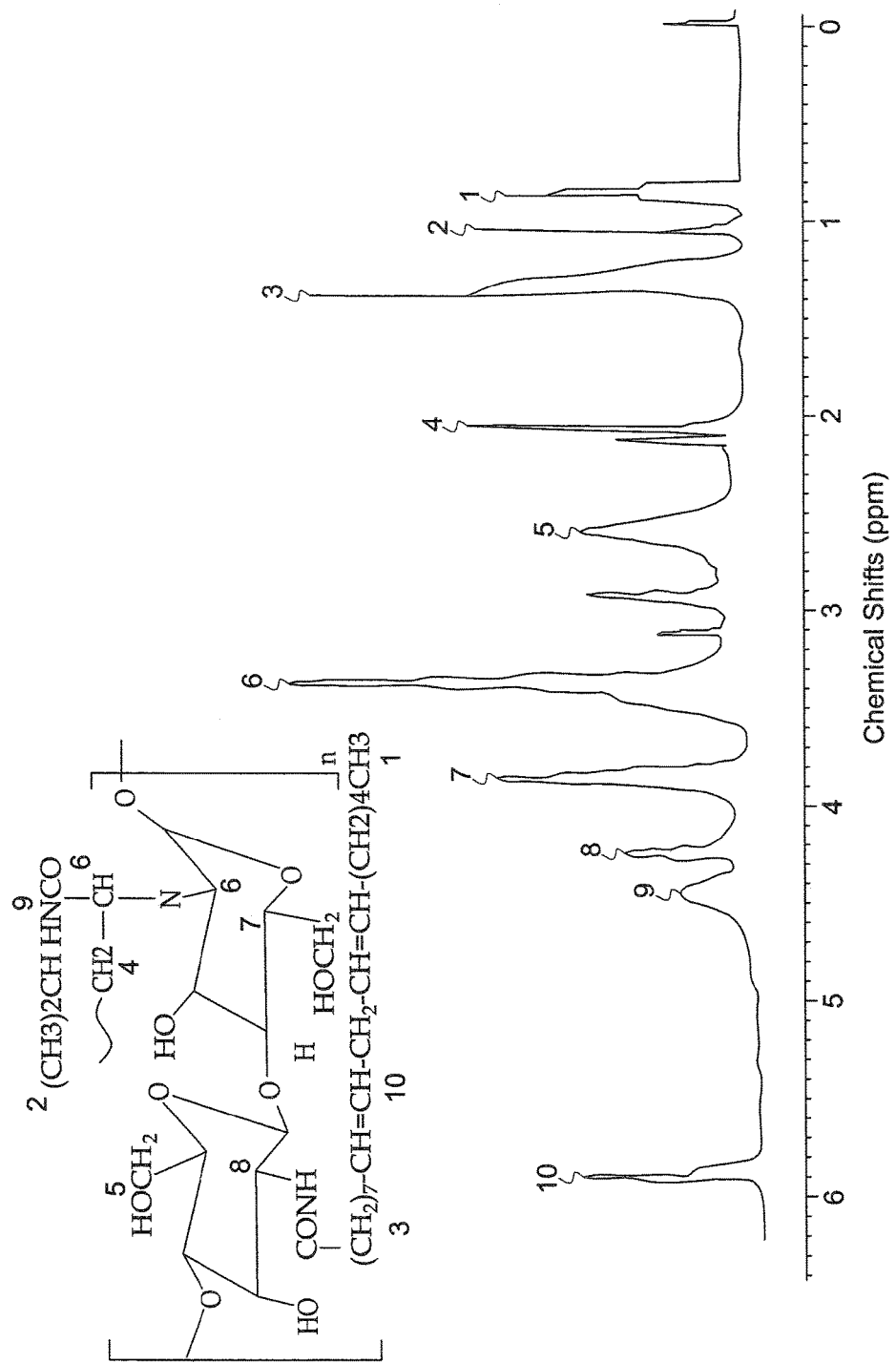
FIG. 4 shows the $^1$H-NMR spectrum of chitosan-linoleic acid (CSLA)-NIPAm (N-Isopropylacrylamide).

The second step is to prepare amphiphilic chitosan after modification with fatty or amino acids by grafting of CSOA or CSLA with NIPAm. The reaction was completed through radical polymerization as represented in FIGS. 1 and 2. The chemical structures and the grafting degree of substitution of CSOA-NIPAm can be determined from $^1$H-NMR analysis. The $^1$H-NMR spectrum of CSOA-NIPAm was selected and represented in FIG. 4. The grafting percentages can be determined by comparing the integration intensity of CONH (1H) of NIPAm and CH=CH group of OA and LA that appeared at 4.23 and 5.93 ppm respectively. The grafting degree of CSOA-NIPAm, CSLA-NIPAm and CSG-NIPAm were 20.8, 25.4 and 15.3%, respectively. This data indicated that approximately 25 and 10% and 5% of amine groups of CSOA, CSLA CSG were not amidated or grafted onto CS.

Figure 5:
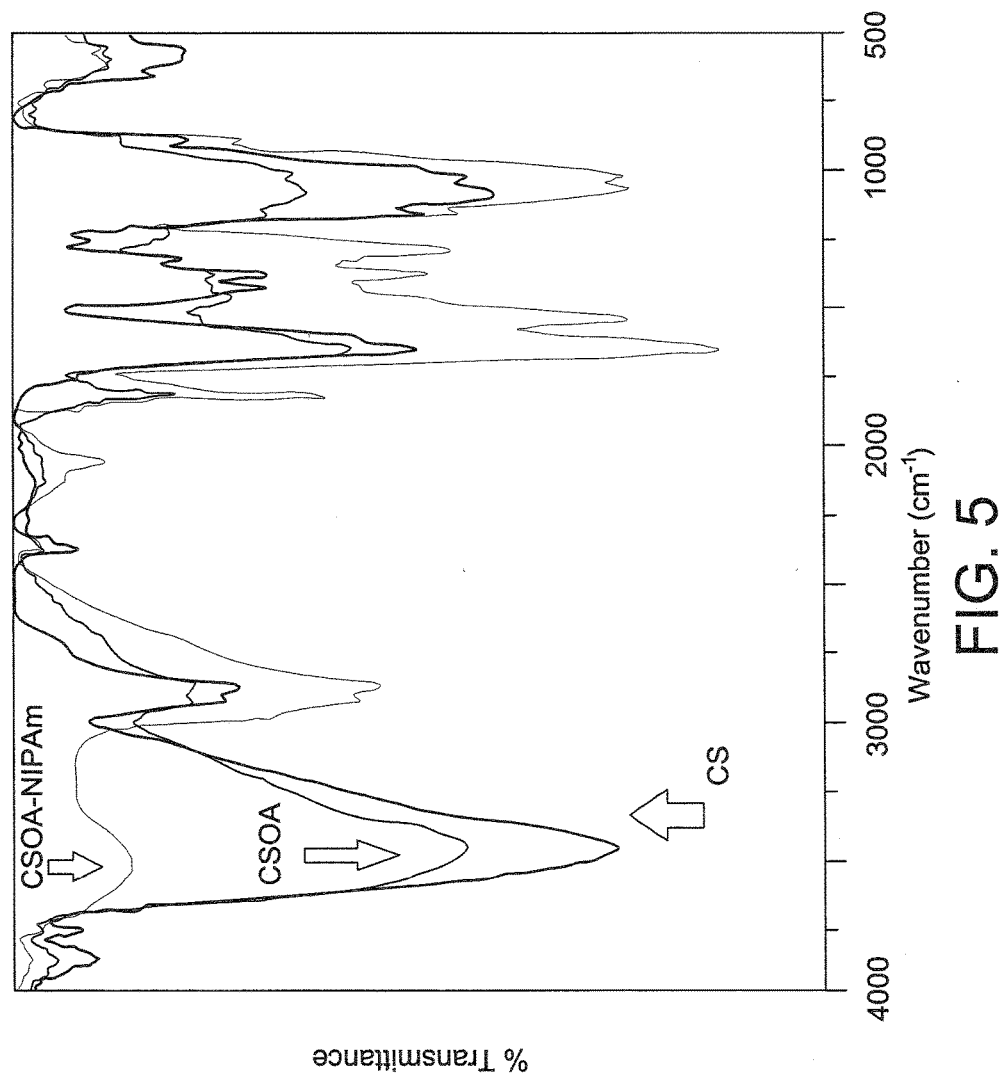
FIG. 5 shows the FTIR spectra of A) chitosan (CS), B) chitosan oleic acid (CSOA) and C) CSOA-NIPAm graft.

The grafting of CS with fatty acids, amino acids and NIPAm was confirmed using the FT-IR spectroscopy as shown in FIG. 5, which shows the spectra of CS, CSOA and CSOA-NIPAm graft. The characteristic absorptions of CS are: 3400 cm$^{-1}$ (O—H stretching); 2900 cm$^{-1}$ (C—H stretching); 1560 cm$^{-1}$ (amide I); 1400 (amide II); absorption bands at 1160 cm$^{-1}$, 1083 cm$^{-1}$ and 1030 cm$^{-1}$ (C—O stretching) were characteristics of its saccharine structure (FIG. 5A). The new characteristic bands of NIPAm are: 3342 cm$^{-1}$ (C—H stretching), 1652 and 1538 cm$^{-1}$ (amide bands), and 1360 cm$^{-1}$ (methyl groups) and observed in the FTIR spectrum of CSOA-NIPAm.

Figure 6:
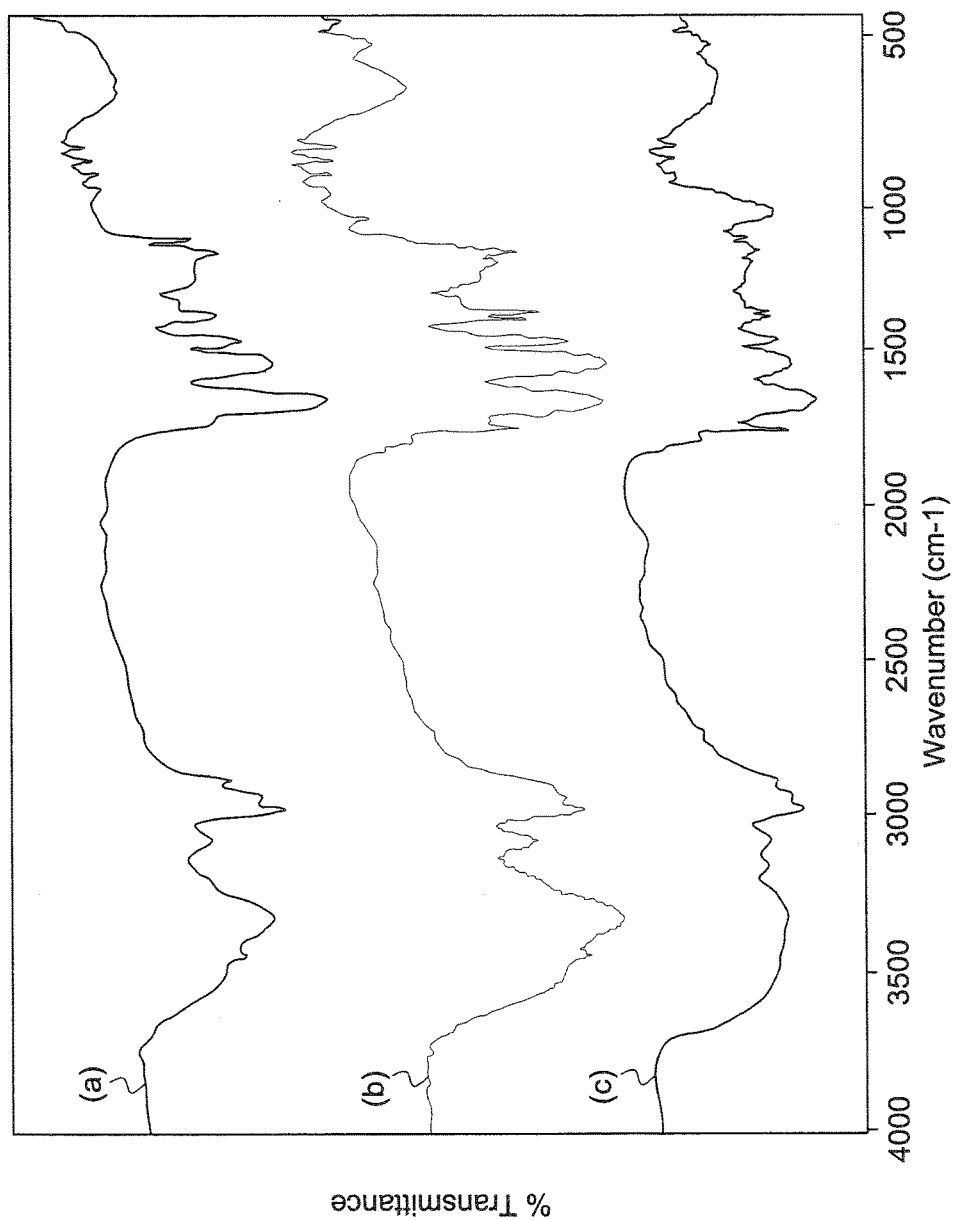
FIG. 6 shows the FTIR spectra of A) CSOA-NIPAm, B) CSLA-NIPAm and C) CSG-NIPAm nanoparticles respectively.

The third step to prepare amphiphilic CS nanoparticles is based on ionic gelation of modified CS on solvent evaporation method or crosslinking polymerization at temperature more than LCST of NIPAm without surfactants. In this respect, methylene chloride was selected due to high rapid rate ability to diffuse into the aqueous phase as non-solvent facilitating particle formation upon evaporation. The aqueous solutions of (1% $CH_3COOH$) CSLA-NIPAm and CSG-NIPAm grafts were held under vacuum for 30 min at 20° C. to remove methylene chloride followed by addition of 1 mL of 0.25% sodium tripolyphosphate (TPP) solution was added as a crosslinking reagent. The volume percentage of methylene chloride was increased from 1 and 10% for CSLA-NIPAm and CSG-NIPAm to form slightly turbid solution. The percentages of methylene chloride for CSLA-NIPAm and CSG-NIPAm were changed according to the solubility of CSLA-NIPAm and CSG-NIPAm in aqueous solutions and degree of unsaturation of LA. The methylene chloride as solvent accelerates the micelle formation of CSLA-NIPAm and CSG-NIPAm in which their linoleyl and isopropyl groups (NIPAm) directed to the interior due to hydrophobic interaction between these groups. The hydrophilic groups directed to exterior of micelles due to hydrogen bond interaction with water. After the methylene chloride was removed by vaporization under vacuum, the ordered micelles were formed with the linoleyl and oleyl groups. It was expected that the remaining amine of CSLA-NIPAm and CSG-NIPAm micelle will quaternize with $CH_3COOH$ to form acid salt which crosslinked by forming a complex with TPP as represented in FIG. 1. The chemical structure of the crosslinked CSLA-NIPAm and CSG-NIPAm was confirmed by FTIR analysis. In this respect, spectrum of CSLA-NIPAm and CSG-NIPAm nanoparticles was selected as representative sample and illustrated in FIG. 6. FIG. 6 shows the FTIR spectra of a) CSOA-NIPAm, b) CSLA-NIPAm, and c) CSG_NIPAm nanoparticles. It was observed that the characteristic spectrum of the crosslinked polymer is almost the same as the grafted polymer. The slight shift of absorption bands to lower wavenumbers indicated the higher interactions between functional groups which refereed to crosslinking.

Figure 7A:
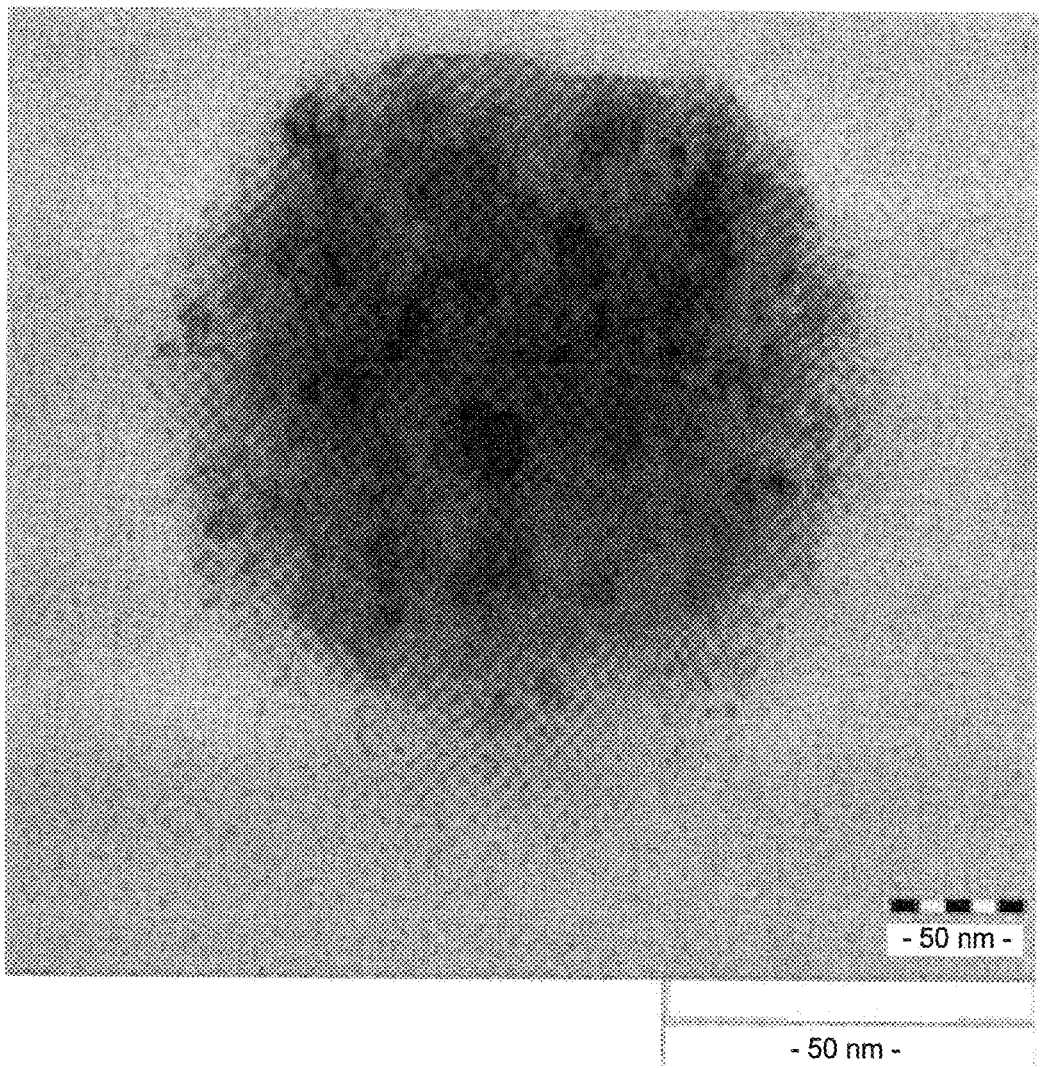
FIG. 7A-B shows the TEM micrographs of A CSMOA-NIPAm and FIG. 7C-D shows the micrograph of CSG-NIPAm particles crosslinked using TTP and MBA, respectively.
Figure 7B:
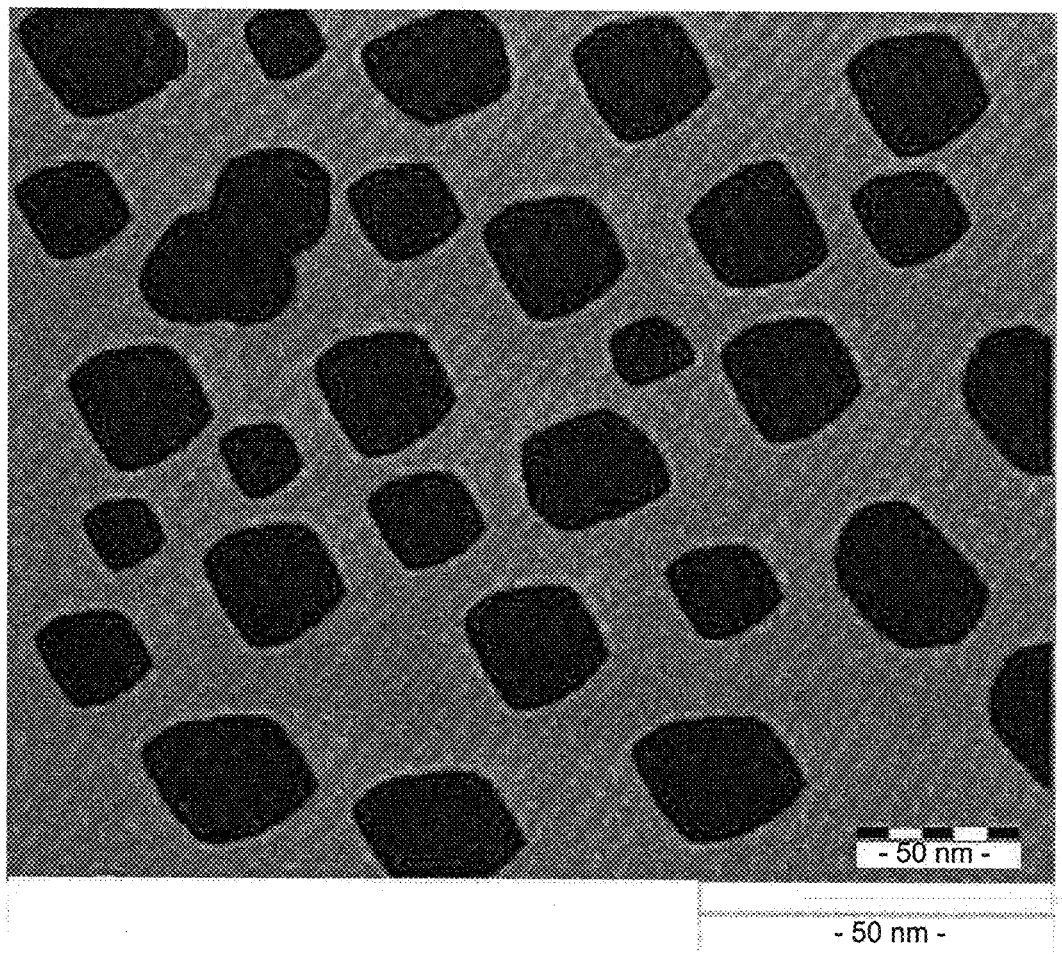
Figure 7C:
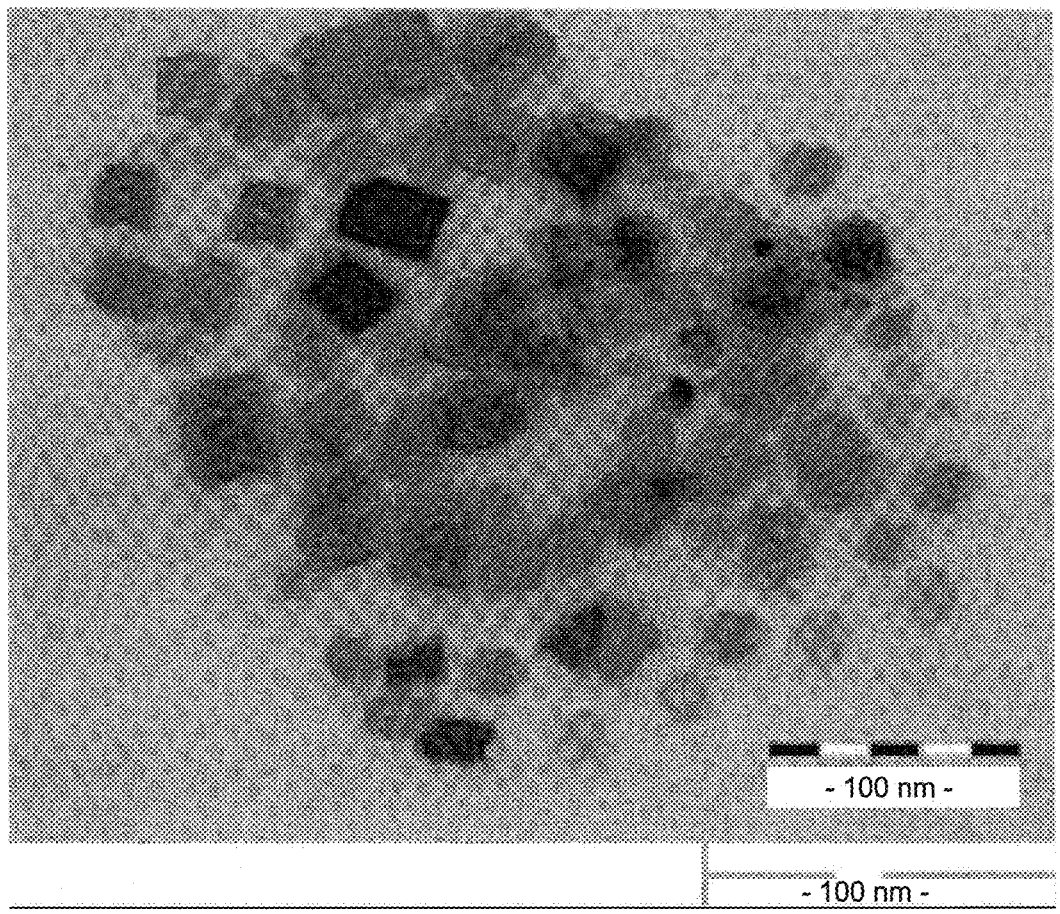
Figure 7D:
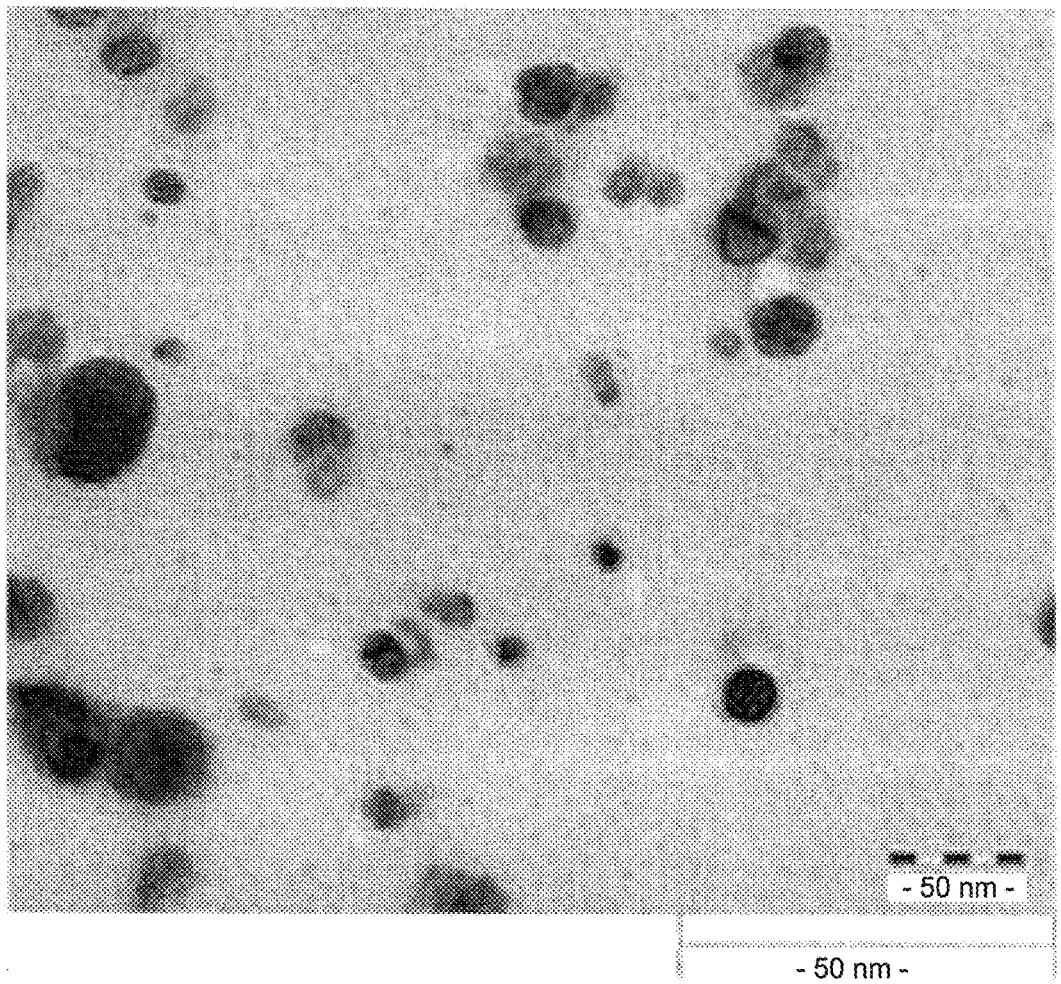
Figure 8A:
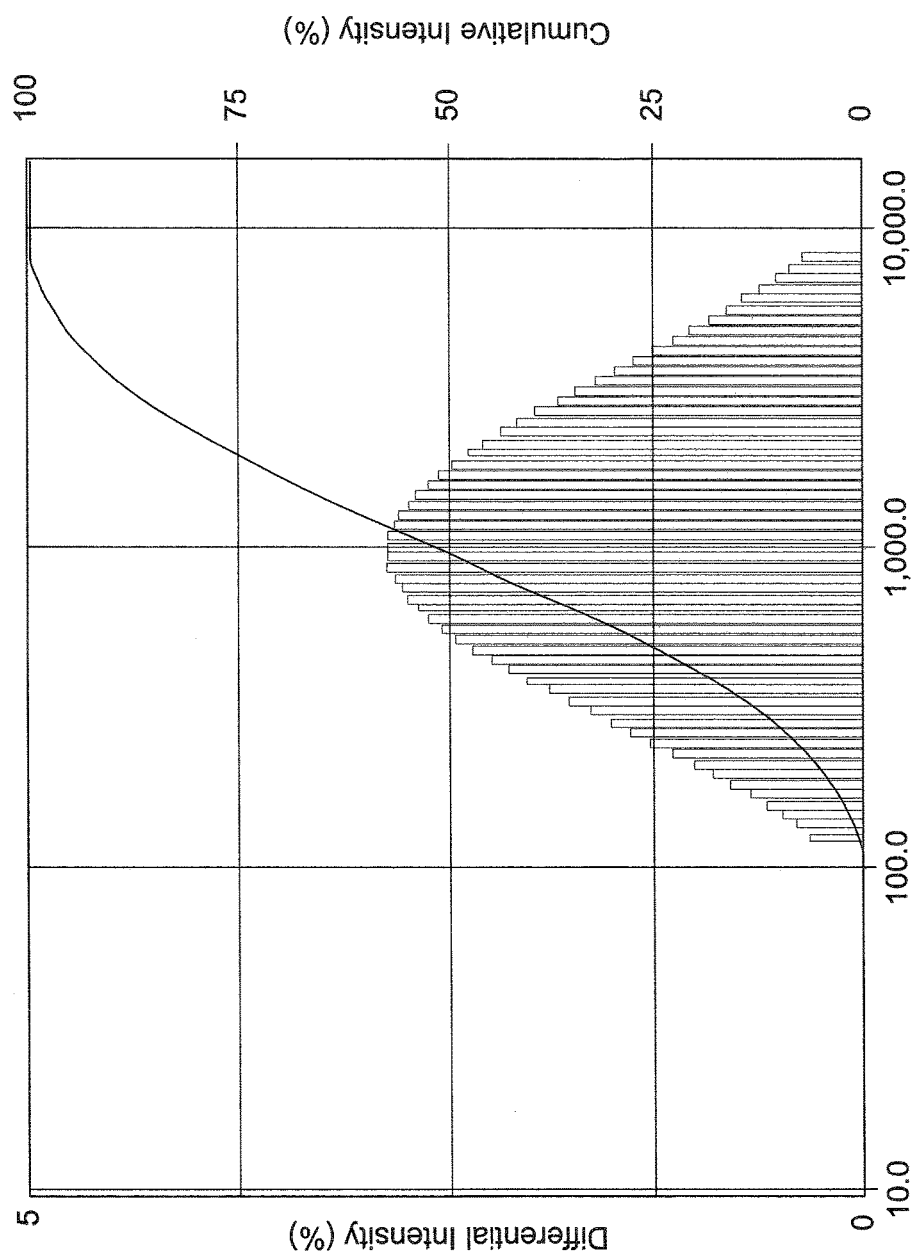
FIG. 8A-C shows the dynamic light scattering (DLS) measurement of CSG-NIPAm crosslinked with TPP at 25° C. in water.
Figure 8B:
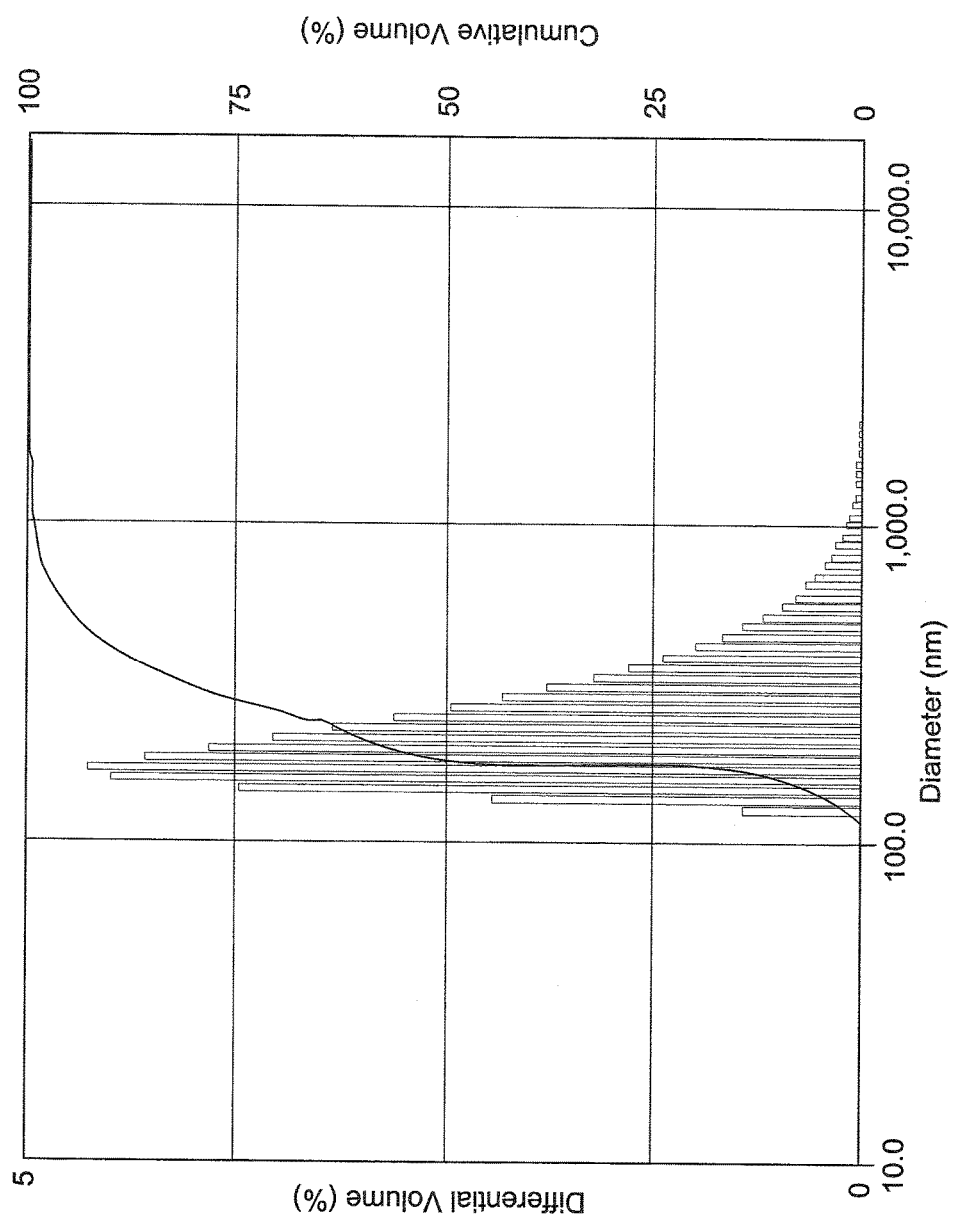
Figure 8C:
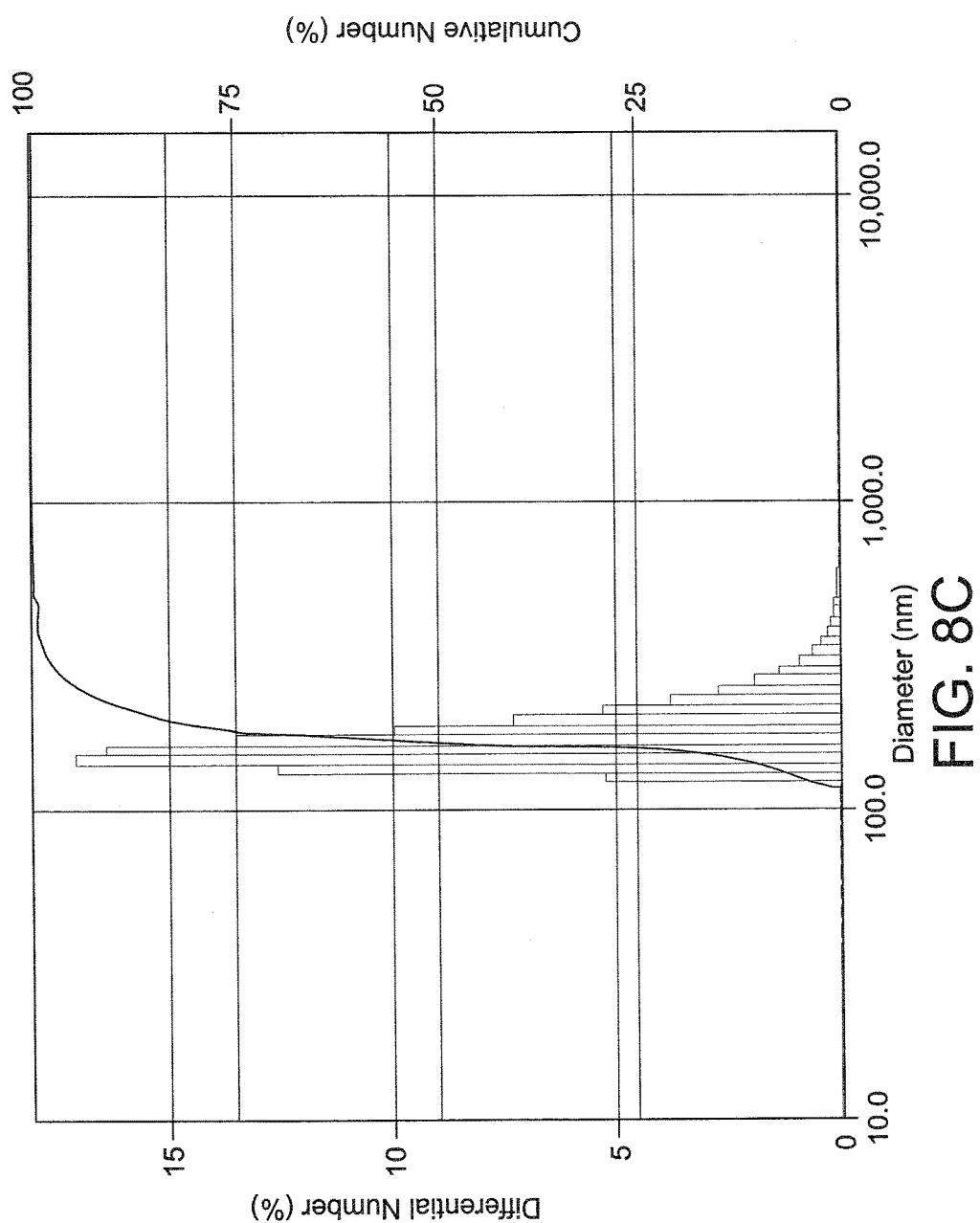
Figure 9A:
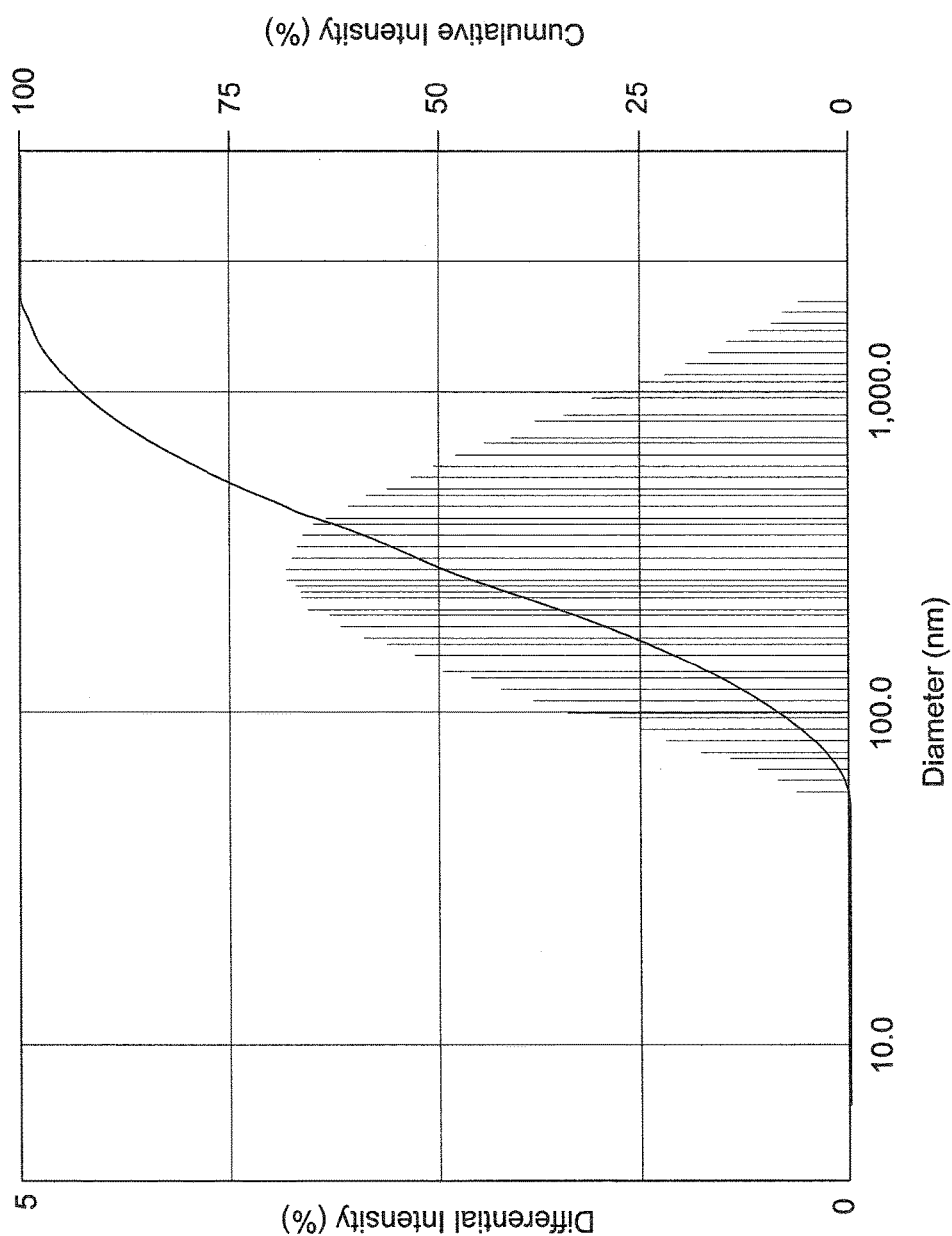
Figure 9C:
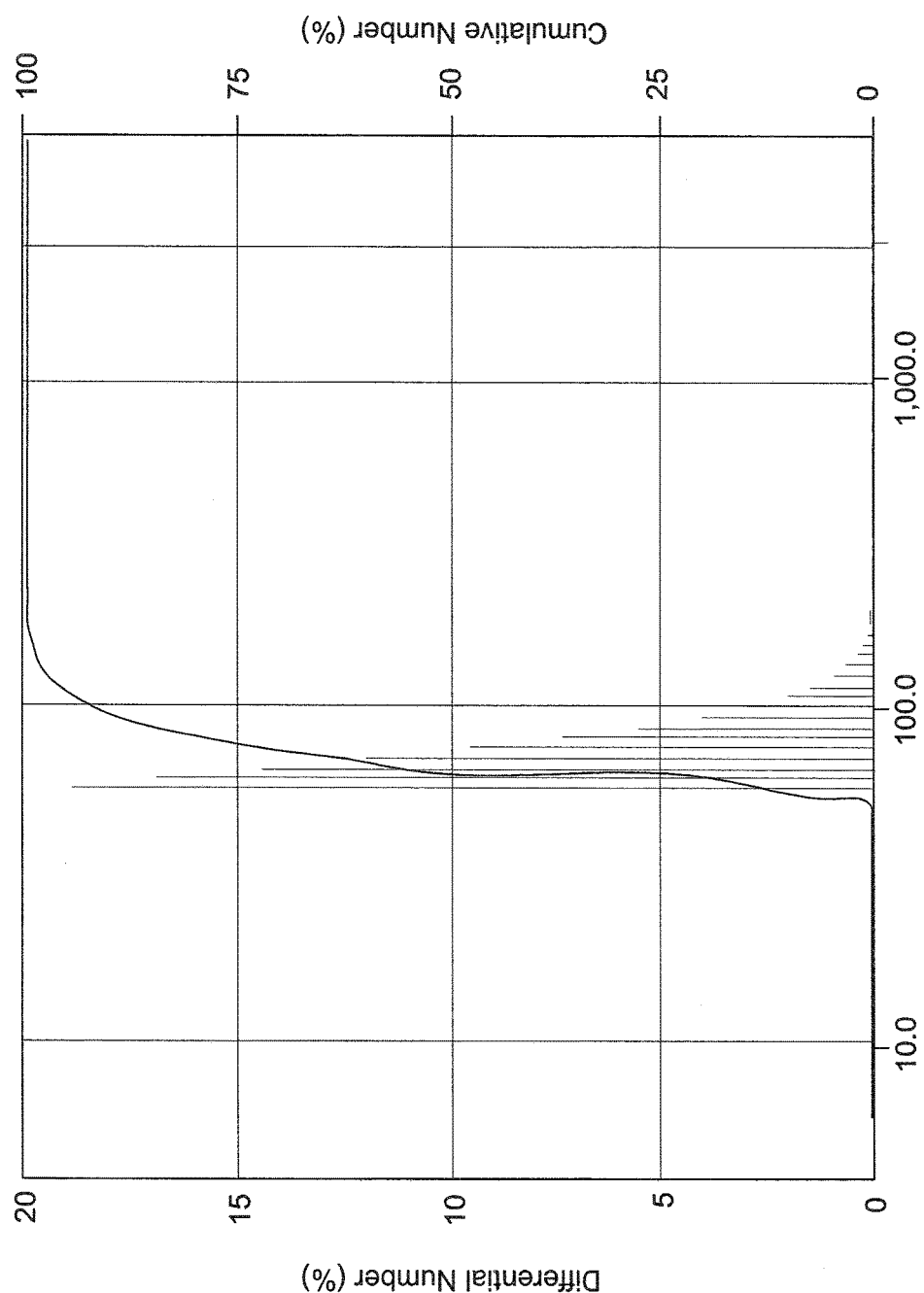
Figure 10B:
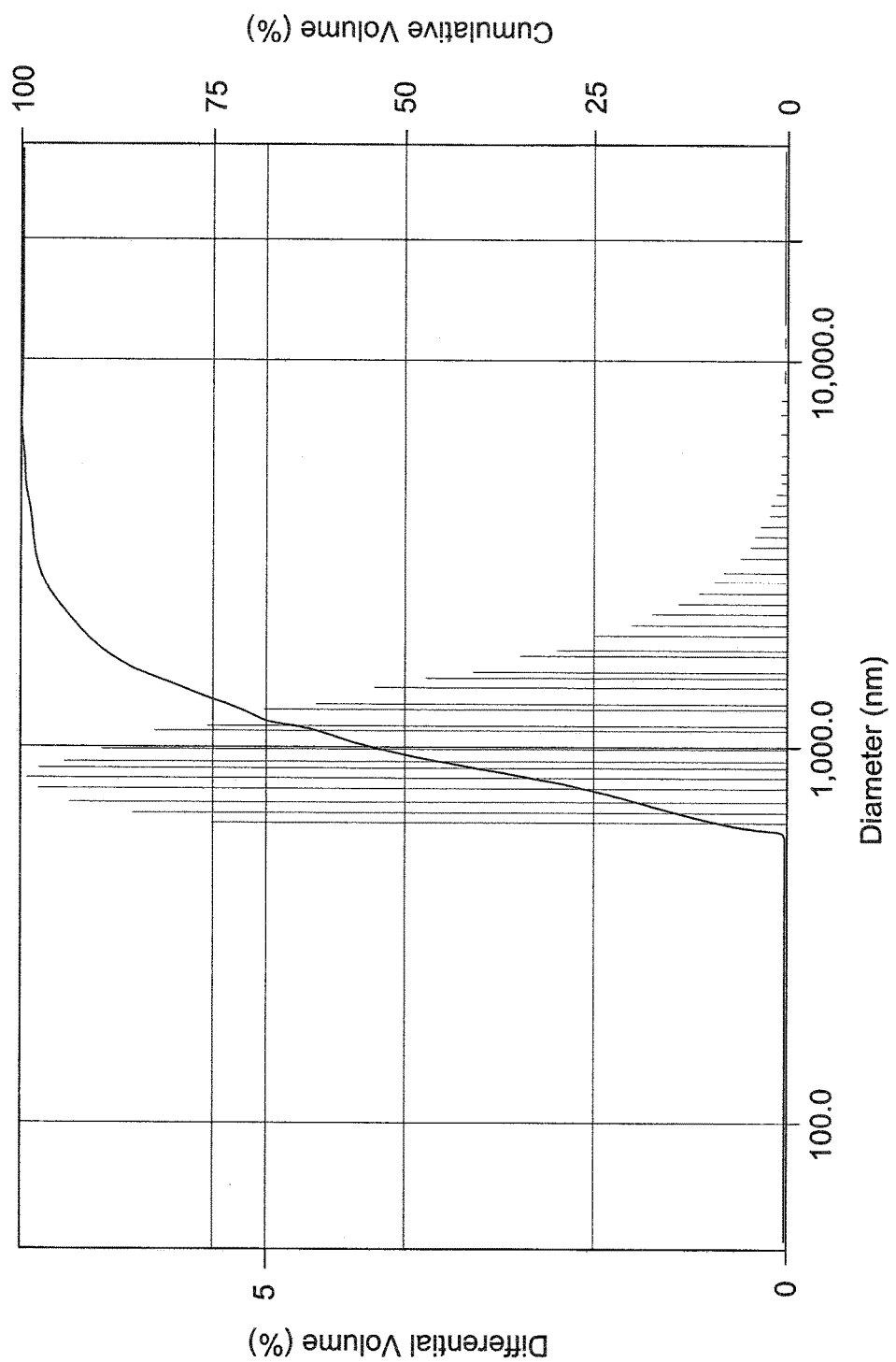
Figure 10C:
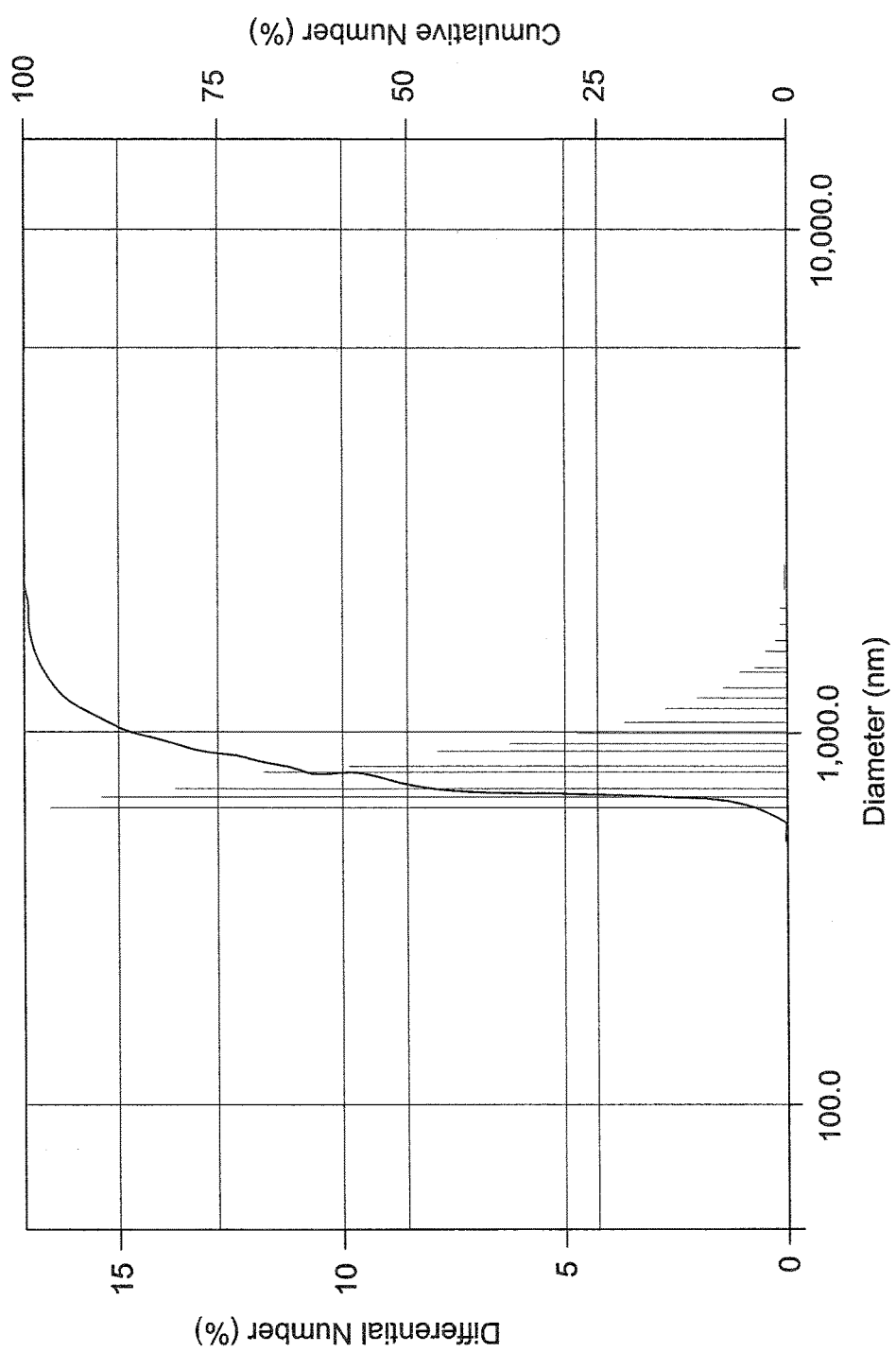
Figure 11A:
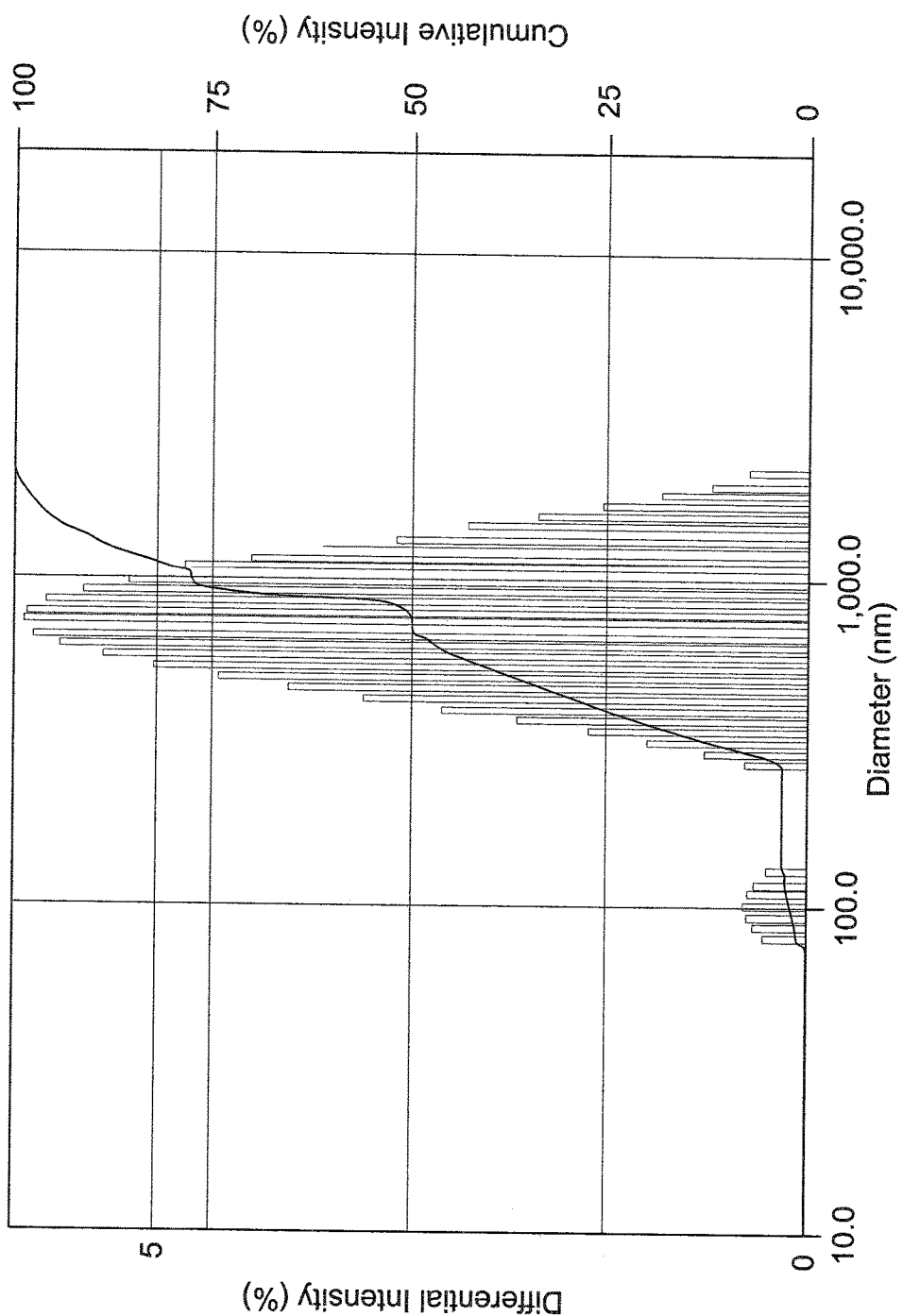
FIG. 11A-C shows the DLS measurement of CSOMA-NIPAm crosslinked with MBA at 25° C. in water.
Figure 11B:
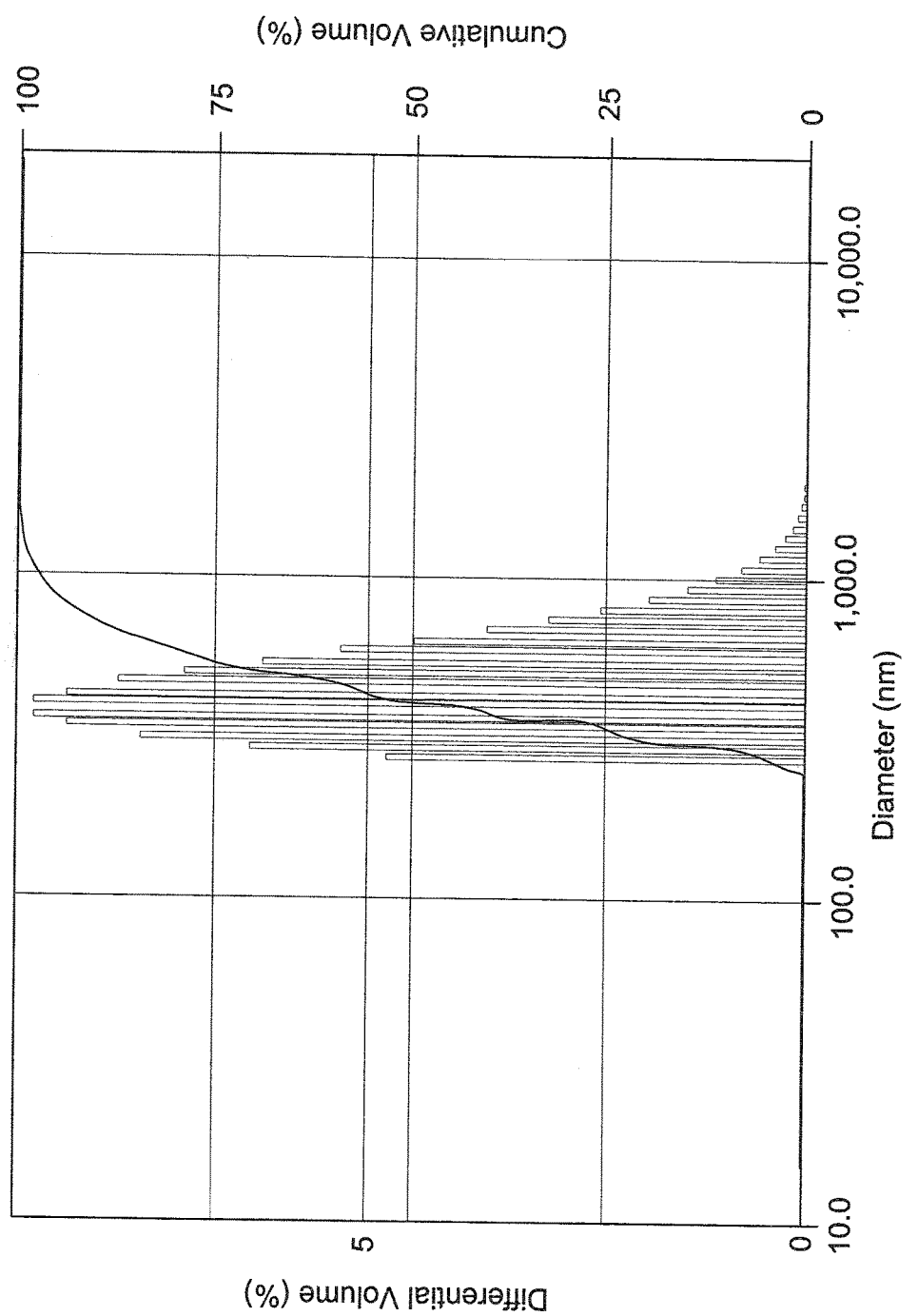
Figure 11C:
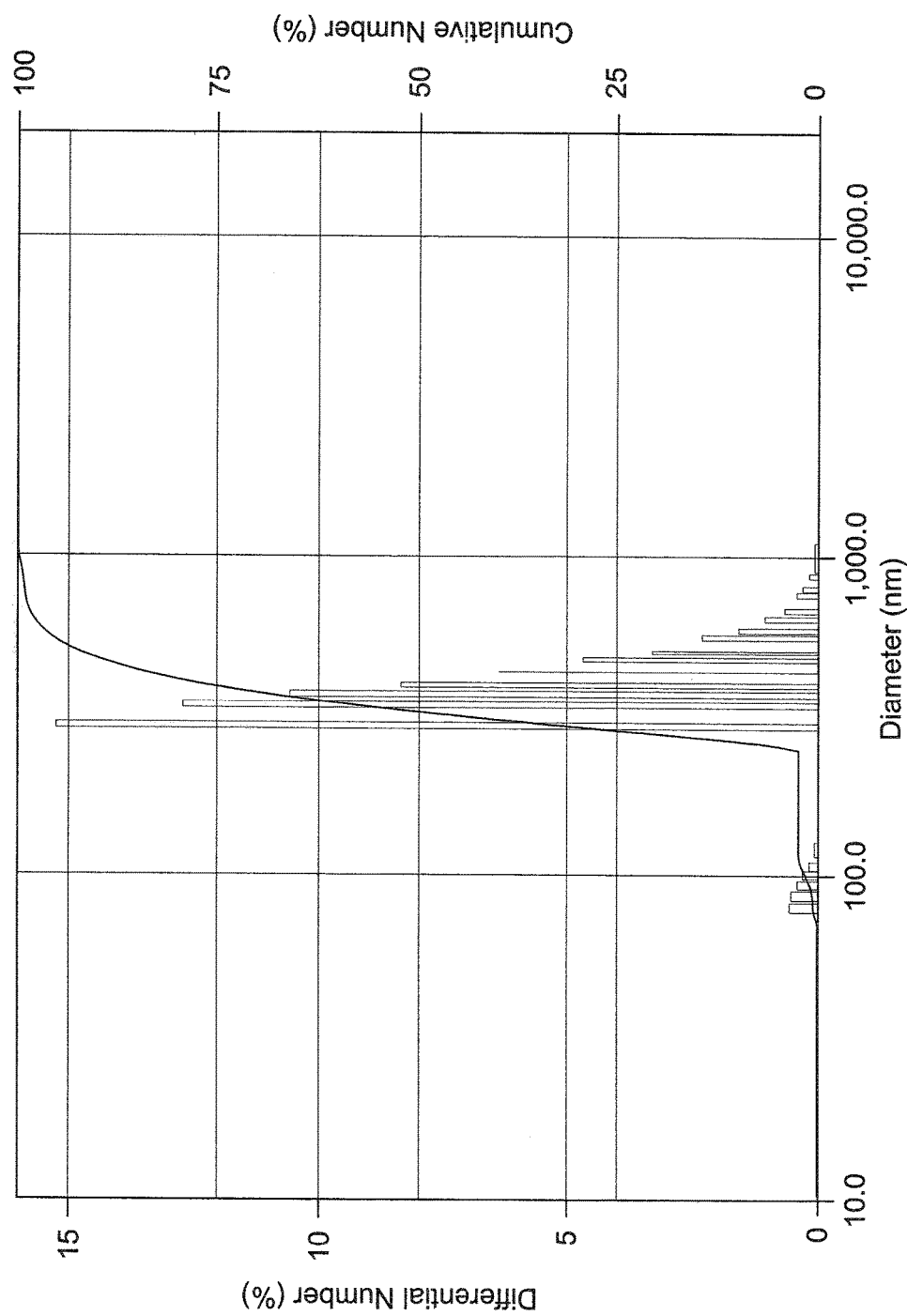

It is very important to determine the morphology and particle size of the modified CS nanoparticles, which are valuable to discuss the insulin adsorption and release. In this respect, TEM micrographs of CSG-NIPAm and CSMOA-NIPAm prepared by ionic gelation and radical crosslinking were represented in FIG. 7A-D. The micrographs of FIGS. 7B and 7D indicate that the radical crosslinking of modified CS with MBA showed spherical or stretched spherical morphologies and dispersed nanoparticles which indicates the radical crosslinking is more effective to obtain nanoparticles. The morphologies of modified CS-NIPAm particles crosslinked with TPP (FIGS. 7 A and C) showed the formation of clusters and aggregates when ionic gelation is used to obtain microgels as illustrated in FIG. 1. It was also noticed that the modification of CS with amino acids produces uniform nanoparticles more than that modified with fatty acids.

The particle size diameters and polydispersity index (PDI) were determined from dynamic light scattering (DLS) measurements and illustrated in FIGS. 8A-11. All modified CS NIPAm particles have PDI below 0.7 which indicates the formation of monodisperse particles. It was also noticed that the particle diameters were increased in DLS measurements than that observed from TEM micrographs (FIGS. 8A-8C) which indicate that the micro and nanoparticles swelled in water and increase their size from nano to micro scales. This speculation was confirmed from the lower particle sizes of CS modified with fatty acids more than that modified with amino acids due to increased hydrophobicity of particles.

Figure 12:
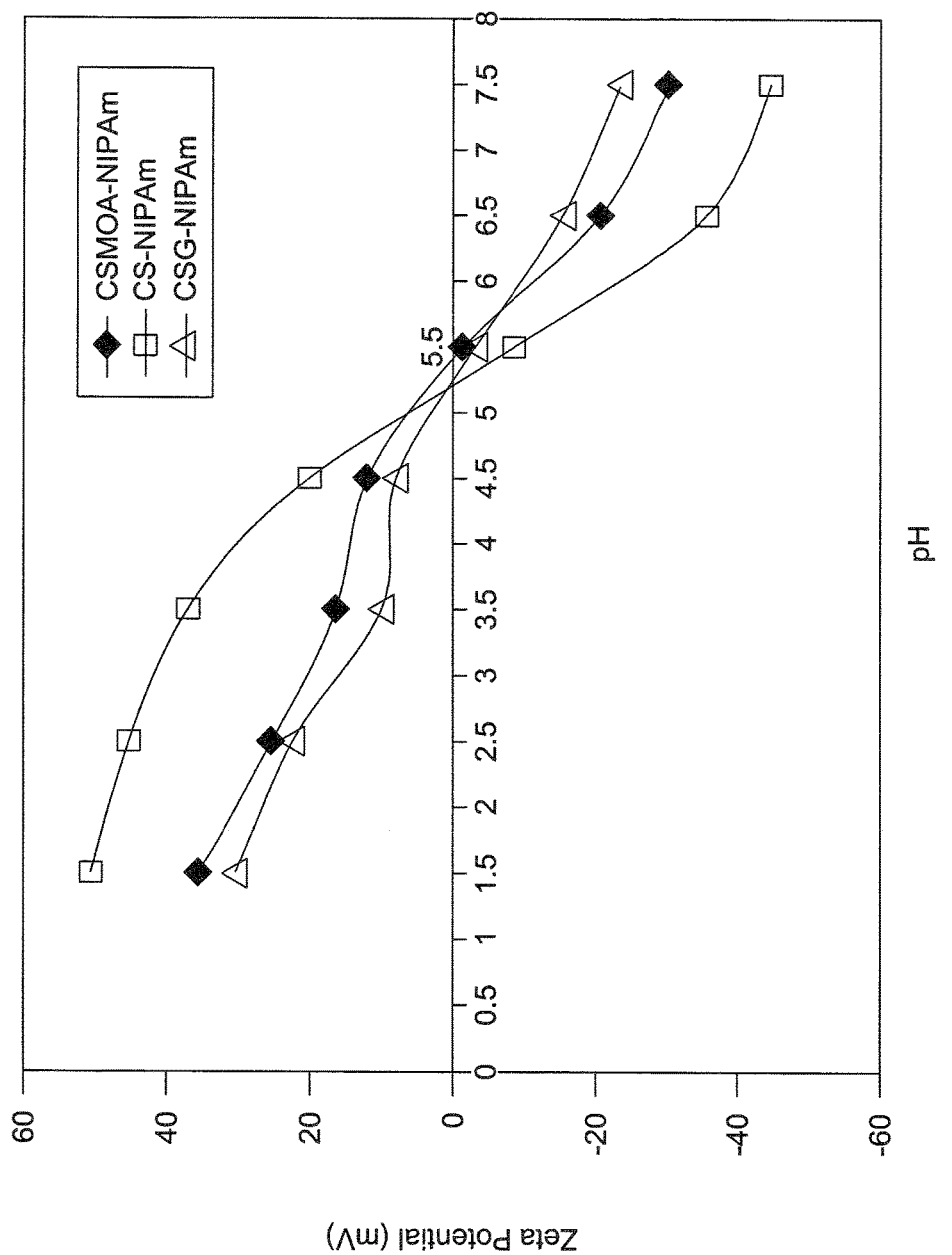
FIG. 12 shows the Zeta potential of modified CS particles crosslinked with MBA at different pH in aqueous solutions at 25° C.

Zeta potentials or surface charges of particles are important parameters that are used to determine the applicability of materials drug delivery. It was reported that the particles used for insulin delivery should possess negative charges to assist for adsorption of insulin to body cells. Moreover, particles having high positive or negative values more than 25 mV showed higher dispersability into fluids. The zeta potentials (mV) of CS nanoparticles were determined at different pH levels, ranging from 1.5 to 7.4 and are represented in FIG. 12. The data confirmed that the crosslinked modified CS-NIPAm nanoparticles using MBA have values more than −45 mV at pH 7.4 which indicate the high dispersability of particles in fluids. The isoelectric points of particles ranged from pH 5.2 to 5.7.

The insulin suspension was loaded into the modified CS nanoparticles as illustrated in the experimental section and the loading capacity (Q, mg/g) was determined and listed in Table 1. The loading capacity data indicated that both modified CS with fatty and amino acids with NIPAm grafts using radical crosslinking with MBA have high loading capacity more than that crosslinked with ionic gelation by TPP. These results were referred to lower particle size and higher interaction between insulin and crosslinked CS networks.

TABLE 1

Insulin Loading Capacity of Modified CS Nanoparticles at 20° C.

| Material | CS-NIPAm-MBA | CSOA-TPP | CSG-TPP | CSG-NIPAm-MBA | CSG-NIPAm-TPP | CSOMA-TPP | CSLMA-TPP | CSOMA-NIPAm-MBA |
|---|---|---|---|---|---|---|---|---|
| Q mg/g | 25 | 25.7 | 32.2 | 36 | 29 | 30 | 30.76 | 39.1 |

Figure 13:
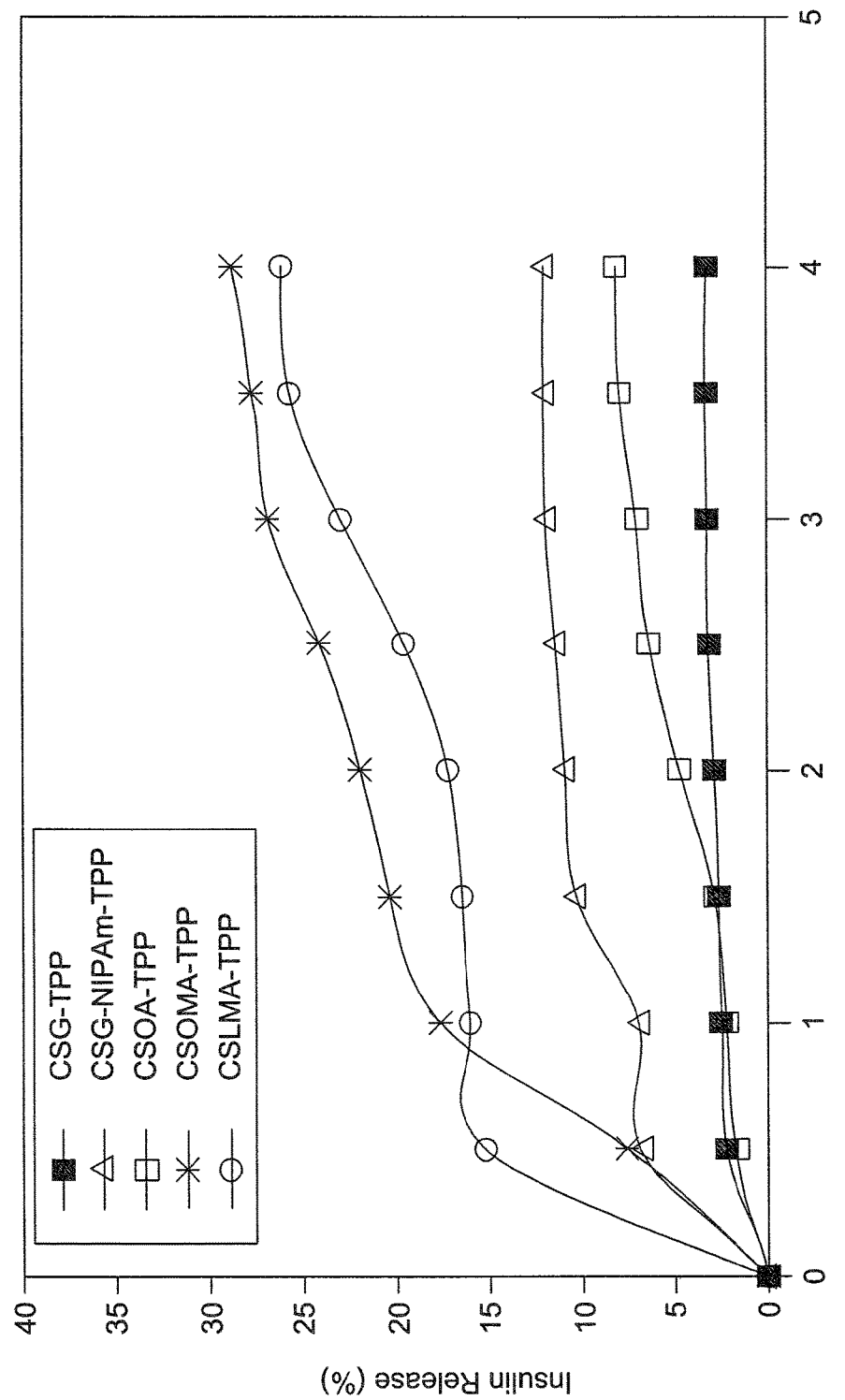
FIG. 13 shows the insulin release % of modified CS nanoparticles crosslinked using TPP at 37° C. in stomach fluid (pH=1.5).
Figure 14:
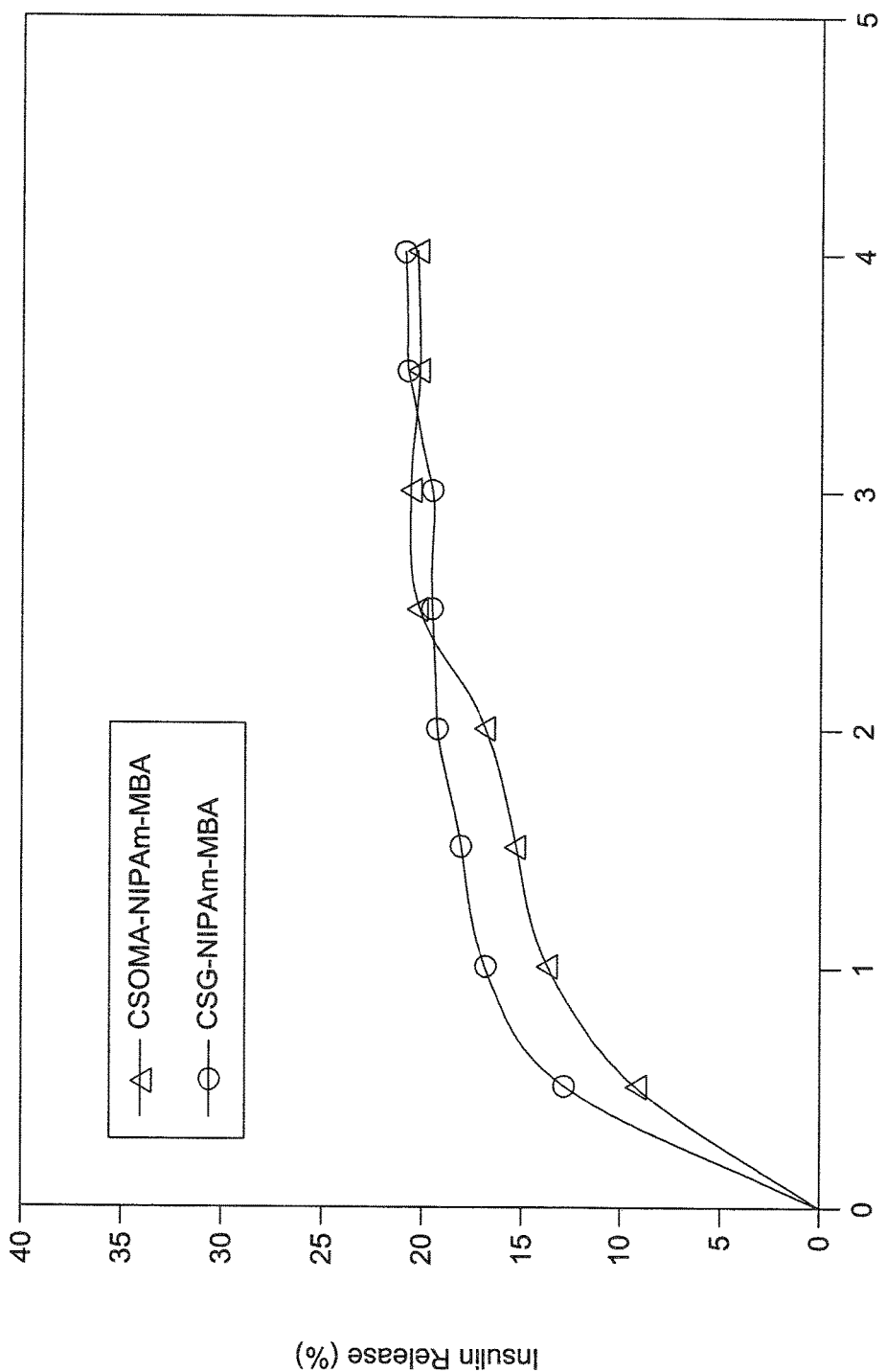
FIG. 14 shows the insulin release % of modified CS nanoparticles crosslinked using MBA at 37° C. in stomach fluid (pH=1.5).

The insulin release data were investigated at 37° C. after drying the modified CS nanoparticles including insulin at different pHs. The stomach fluid with pH 1.5 was used to study the release of insulin in the stomach. The data were represented in FIGS. 13 and 14. The insulin release (%) data indicated that both modified CS with fatty and amino acids with NIPAm grafts using radical crosslinking with MBA released insulin at a pH less than that crosslinked with ionic gelation by TPP. The modified CS with fatty acids release approximately 5% from insulin for 5 h. It was also noticed that the maximum insulin release (%) for the modified CS was not increased more than 25% in the stomach fluid. These data indicated that the modified CS nanoparticles resist the stomach fluid.

Figure 15:
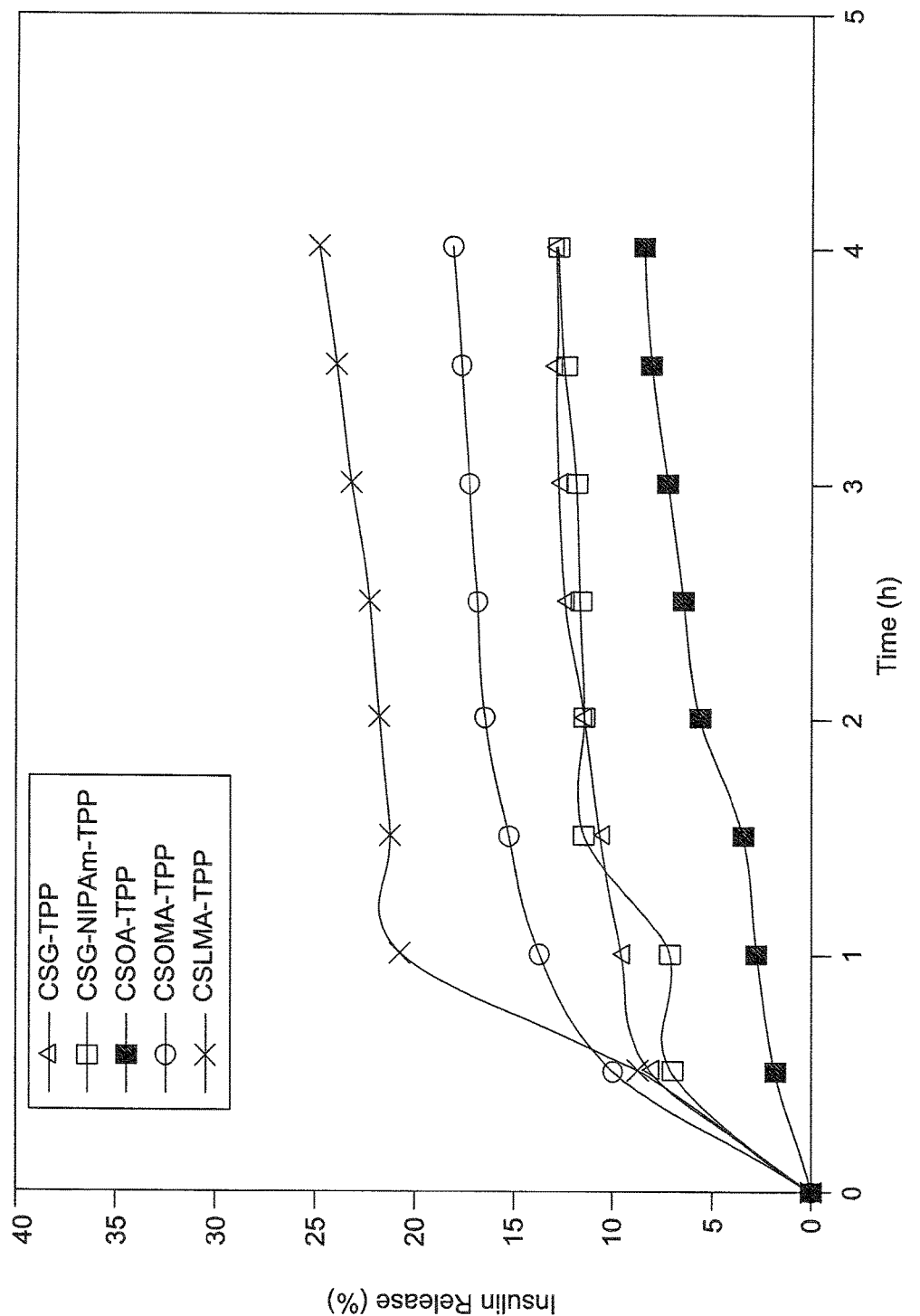
FIG. 15 is a plot of the insulin release % of modified CS nanoparticles crosslinked using TPP at 37° C. in bile salts fluid (pH=7.4).
Figure 16:
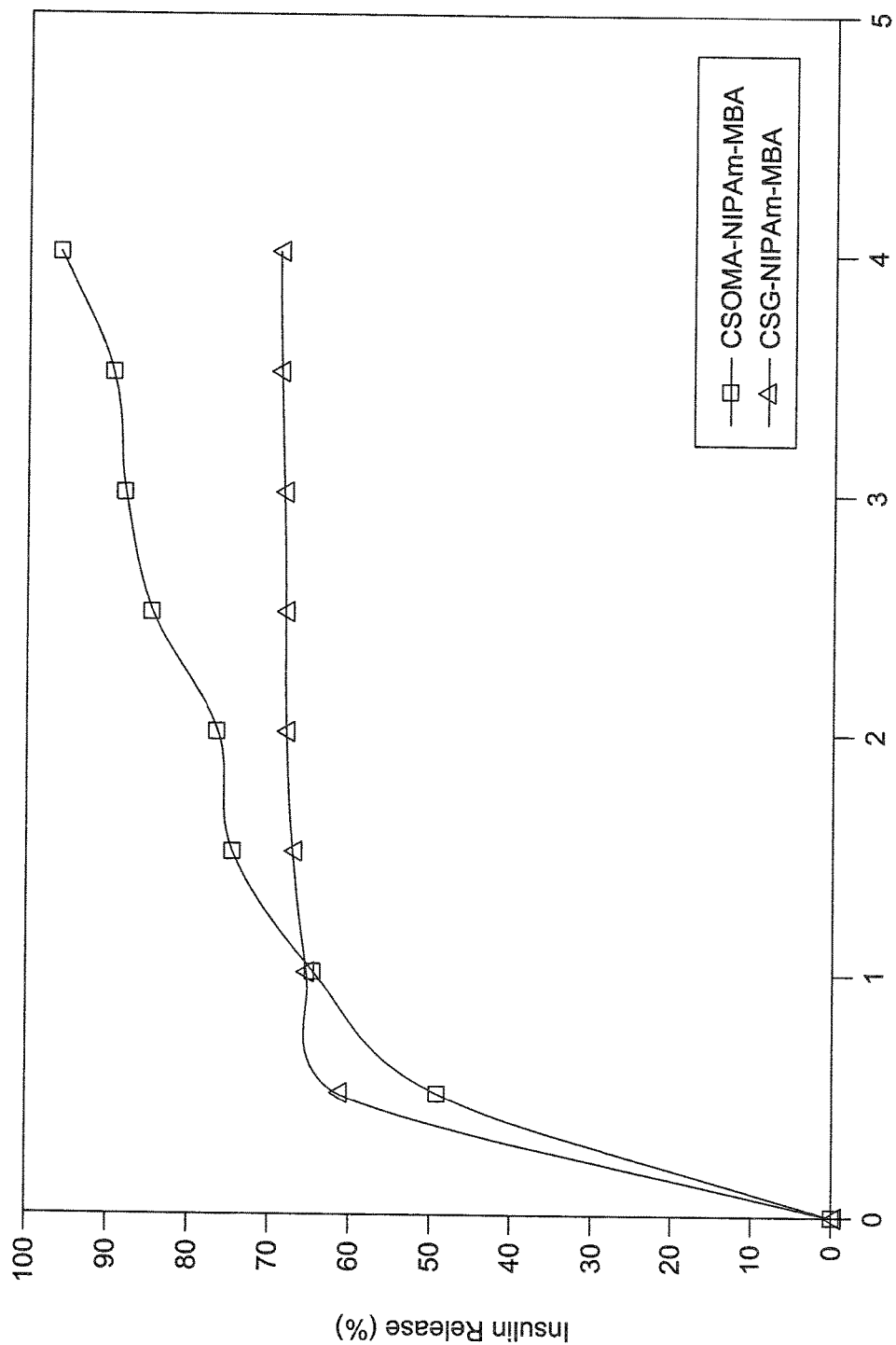
FIG. 16 shows the plot of the insulin release % of modified CS nanoparticles crosslinked using TPP at 37° C. in bile salts fluid (pH=7.4).

The bile salts fluid with pH 7.4 was used to study the release of insulin in the intestine. The data is represented in FIGS. 15 and 16. The insulin release (%) data indicated that both CSG-NIPAm-MBA and CSOMA-NIPAm-MBA released (50%) of insulin after 30 minutes. The insulin released completely after 4 h using CSOMA-NIPAm-MBA. These data indicated that the modified CS nanoparticles can be used for oral insulin diabetic treatments.

It is to be understood that the present invention is not limited to the embodiments described above, but encompasses any and all embodiments within the scope of the following claims.

We claim:

1. A method of synthesizing modified chitosan particles for oral insulin delivery comprising:
    providing chitosan dissolved in acidic solution to provide a chitosan solution;
    adding an amidating agent to the chitosan solution, the amidating agent including a fatty acid or an amino acid to provide a first reaction mixture;
    adding an activating agent to the first reaction mixture;
    stirring the reaction mixture until an amidated chitosan precipitate is formed;
    combining the amidated chitosan with N-Isopropylacrylamide (NIPAm) in water to form a second reaction mixture;
    adding the reaction mixture to a solution including a coupling agent to graft the amidated chitosan with the N-Isopropylacrylamide (NIPAm) and provide amidated chitosan grafted with N-Isopropylacrylamide (NIPAm);
    cross-linking the amidated chitosan grafted with N-Isopropylacrylamide (NIPAm) to provide the modified chitosan particles; and
    loading insulin onto the modified chitosan particles.

2. The method of synthesizing modified chitosan particles for oral insulin delivery according to claim 1, further comprising washing and drying the amidated chitosan precipitate.

3. The method of synthesizing modified chitosan particles for oral insulin delivery according to claim 1, wherein the activating agent is 1-ethyl-3-(3-dimethylaminopropyl) carbodiimide (EDC).

4. The method of synthesizing modified chitosan particles for oral insulin delivery according to claim 1, wherein a mole ratio of the fatty acid or the amino acid to the activating agent is 1:1.

5. The method of synthesizing modified chitosan particles for oral insulin delivery according to claim 1, wherein the fatty acid or the amino acid is coupled to an amine group of the chitosan.

6. The method of synthesizing modified chitosan particles for oral insulin delivery according to claim 1, wherein the coupling agent is 3-aminopropyltriethoxyxilane (APS).

7. The method of synthesizing modified chitosan particles for oral insulin delivery according to claim 1, wherein the second reaction mixture further includes a cross-linking agent.

8. The method of synthesizing modified chitosan particles for oral insulin delivery according to claim 7, wherein the cross-linking agent is N,N-methylene bisacrylamide (MBA).

9. The method of synthesizing modified chitosan particles for oral insulin delivery according to claim 1, wherein the crosslinking includes ionic gelation.

10. The method of synthesizing modified chitosan particles for oral insulin delivery according to claim 9, wherein the ionic gelation includes:
- dissolving the amidated chitosan grafted with N-Isopropylacrylamide (NIPAm) in acidic solution;
- adding an organic solvent to the solution until a turbid solution is formed;
- adding a crosslinking agent to the turbid solution to provide modified chitosan particles; and
- isolating the modified chitosan particles.

11. The method of synthesizing modified chitosan particles for oral insulin delivery according to claim 10, wherein the acidic solution is 0.1 M acetic acid solution, the organic solvent is methylene chloride, and the cross-linking agent is sodium tripolyphosphate 8% w/v solution (TPP).

12. A method of synthesizing modified chitosan particles for oral insulin delivery comprising:
- providing chitosan dissolved in acidic solution to provide a chitosan solution;
- adding an amidating agent to the chitosan solution, the amidating agent including a fatty acid or an amino acid to provide a first reaction mixture;
- adding an activating agent to the first reaction mixture;
- stirring the reaction mixture until an amidated chitosan precipitate is formed;
- combining the amidated chitosan with N-Isopropylacrylamide (NIPAm) in water to form a second reaction mixture;
- adding the reaction mixture to a solution including a coupling agent to graft the amidated chitosan with the N-Isopropylacrylamide (NIPAm) and provide amidated chitosan grafted with N-Isopropylacrylamide (NIPAm), the coupling agent being 3-aminopropyltriethoxyxilane (APS); and
- cross-linking the amidated chitosan grafted with N-Isopropylacrylamide (NIPAm) to provide the modified chitosan particles.

\* \* \* \* \*